US011167063B2

(12) United States Patent
Cleek et al.

(10) Patent No.: US 11,167,063 B2
(45) Date of Patent: Nov. 9, 2021

(54) POROUS COMPOSITES WITH HIGH-ASPECT RATIO CRYSTALS

(71) Applicant: W. L. Gore & Associates, Inc., Newark, DE (US)

(72) Inventors: Robert L. Cleek, Flagstaff, AZ (US); Edward H. Cully, Flagstaff, AZ (US); Paul D. Drumheller, Flagstaff, AZ (US); Mei Li, Flagstaff, AZ (US); Peter D. Traylor, Flagstaff, AZ (US)

(73) Assignee: W. L. Gore & Associates, Inc., Newark, DE (US)

( * ) Notice: Subject to any disclaimer, the term of this patent is extended or adjusted under 35 U.S.C. 154(b) by 0 days.

(21) Appl. No.: 14/210,162

(22) Filed: Mar. 13, 2014

(65) Prior Publication Data

US 2014/0271775 A1 Sep. 18, 2014

Related U.S. Application Data

(60) Provisional application No. 61/786,244, filed on Mar. 14, 2013.

(51) Int. Cl.
| | | |
|---|---|---|
| *A61F 2/82* | (2013.01) |
| *A61K 9/00* | (2006.01) |
| *A61L 31/12* | (2006.01) |
| *A61L 27/54* | (2006.01) |
| *A61L 27/16* | (2006.01) |
| *A61L 27/34* | (2006.01) |
| *A61K 31/337* | (2006.01) |
| *A61L 29/04* | (2006.01) |
| *A61L 27/56* | (2006.01) |
| *A61L 29/16* | (2006.01) |
| *A61L 29/14* | (2006.01) |
| *A61L 29/08* | (2006.01) |

(52) U.S. Cl.
CPC ............ *A61L 27/54* (2013.01); *A61K 31/337* (2013.01); *A61L 27/16* (2013.01); *A61L 27/34* (2013.01); *A61L 27/56* (2013.01); *A61L 29/041* (2013.01); *A61L 29/085* (2013.01); *A61L 29/146* (2013.01); *A61L 29/16* (2013.01); *A61L 2300/416* (2013.01); *A61L 2300/63* (2013.01); *A61L 2400/18* (2013.01)

(58) Field of Classification Search
CPC ............ A61L 2300/416; A61L 31/146; A61L 2300/63; A61L 29/146; A61L 2420/02; A61L 27/3683; A61L 33/0076; A61L 2300/62; A61L 33/0094; A61L 27/56; A61K 9/7007; A61K 9/0024; A61P 35/00
See application file for complete search history.

(56) References Cited

U.S. PATENT DOCUMENTS

| | | |
|---|---|---|
| 5,102,402 A | 4/1992 | Dror et al. |
| 5,641,566 A | 6/1997 | Kranzler et al. |
| 5,708,044 A | 1/1998 | Branca |
| 5,824,405 A | 9/1998 | Branca et al. |
| 6,221,153 B1 | 4/2001 | Castor et al. |
| 6,541,589 B1 | 4/2003 | Ballie |
| 6,827,737 B2 | 12/2004 | Hill et al. |
| 6,858,644 B2 | 2/2005 | Benigni et al. |
| 7,049,380 B1 | 5/2006 | Chang et al. |
| 7,306,729 B2 | 12/2007 | Bacino et al. |
| 7,462,675 B2 | 12/2008 | Chang et al. |
| 7,531,611 B2 | 5/2009 | Sabol et al. |
| 7,736,739 B2 | 6/2010 | Lutz et al. |
| 8,637,144 B2 | 1/2014 | Ford |
| 2003/0216803 A1 | 11/2003 | Ledergerber |
| 2006/0047311 A1* | 3/2006 | Lutz ..................... A01K 91/00 606/228 |
| 2006/0096523 A1 | 5/2006 | Myerson et al. |
| 2007/0050007 A1* | 3/2007 | Kondyurin .............. A61L 27/16 623/1.13 |
| 2008/0207872 A1* | 8/2008 | Cunningham ........... A61K 8/64 528/397 |
| 2009/0061071 A1 | 3/2009 | McMorrow et al. |
| 2009/0246252 A1 | 10/2009 | Arps et al. |
| 2010/0248324 A1 | 9/2010 | Xu et al. |
| 2010/0268321 A1 | 10/2010 | McDermott et al. |
| 2010/0272773 A1 | 10/2010 | Kangas et al. |
| 2011/0015664 A1 | 1/2011 | Kangas et al. |
| 2011/0082536 A1* | 4/2011 | Cook ...................... A61L 31/10 623/1.15 |
| 2011/0125253 A1* | 5/2011 | Casanova ................. A61F 2/06 623/1.34 |

FOREIGN PATENT DOCUMENTS

| | | |
|---|---|---|
| CN | 102653528 A | 9/2012 |
| CN | 102727464 A | 10/2012 |
| JP | 2011245308 | 12/2011 |
| JP | WO2014163091 | 10/2014 |
| WO | WO96/00103 | 1/1996 |
| WO | WO2007/030512 | 3/2007 |
| WO | WO2009/120361 | 10/2009 |
| WO | WO2011/008393 | 1/2011 |

OTHER PUBLICATIONS

Castro, Javier S, Negative Impact of Paclitaxel Crystallization on Hydrogels and Novel Approaches for Anticancer Drug Delivery Systems, Current Cancel Treatment, pp. 767-782 Dec. 9, 2011.

(Continued)

*Primary Examiner* — Tracy Liu

(57) ABSTRACT

The present disclosure is directed toward composite materials comprising high aspect ratio habits of drug crystals which can be partially or fully extending into a substrate, and additionally, can be projecting from a substrate at an angle of about 20° to about 90°. The present disclosure is directed toward medical devices, such as medical balloons, comprising said composite and methods of using and making the same. The described composite can be used for the local treatment of vascular disease. The present disclosure is also directed toward paclitaxel crystals with a hollow acicular habit.

10 Claims, 28 Drawing Sheets

(56) References Cited

OTHER PUBLICATIONS

Eddleston, Mark D, Formation of Tubular Crystals of Pharmaceutical Compounds, Crystal Growth & Design, vol. 10, 365-370, 2010.
Lee Byung HA, Paclitaxel-coated Expanded Polytetrafluoroethylene Haemodialysis Grafts Inhibit Neointimal Hyperplasia in Porcine Model of Graft Stenosis, Nephrology Dialysis Transplantation, vol. 21, No. 9, pp. 2432-2438, Sep. 2006.
Lee, Preparation and CharaCterization of Solvent Induced Dihydrated, Anhydrous and Amorphous Paclitaxel, Bull Korean Chemical Society, vol. 22, p. 925, 2001.
Luo B, Fabrication of Magnetite Hollow Porous Nanocrystal Shells as a Drug Carrier for Paclitaxel, Journal ofMaterials Chemistry, vol. 20 pp. 7107-7113, Jul. 2, 2010.
Martins, Damien, Formation of Crystalline Hollow Whiskers as Relics of Organic Dissipative Structures, American Chemical Society,Crystal Growth & Design, pp. 3020-3026,2011.
Pyo, S.H., Preparation and dissolution Profiles of the Amorphous, Dihydrated Crystalline, and Anhydrous Crystalline Forms of Paclitaxel, Drying Technology, 25, 1759-1767, 2007.
Yoon, J.W., Establishment of a Solvent Map for Formation of Crystalline and Amorphous Paclitaxel by Solvent Evaporation Process, Korean J Chemical Engineering, 28, 1918-1923, 2011.
International Search Report; PCT/US2014/017253, dated Jul. 31, 2014, 8 pages.
Nam et al., "Reduced burst release from ePTFE grafts: A new coating method for controlled drug release", Bulletin of the Korean Chemical Society, vol. 29, No. 2, 2008, pp. 422-426.

\* cited by examiner

No anneal

ACN

EtOH

MeOH

No anneal

ACN

EtOH

MeOH

No anneal

ACN

EtOH

MeOH

No anneal

ACN

EtOH

MeOH

No anneal

ACN

No anneal

ACN

Water

ACN

Water

ACN

POROUS COMPOSITES WITH HIGH-ASPECT RATIO CRYSTALS

FIELD OF THE DISCLOSURE

The disclosure relates to composites comprising substrates having oriented drug crystals of high aspect ratio habit. In particular, the disclosure relates to said composites, their methods of preparation, devices comprising said composites, and their methods of use, e.g., uses for the treatment of vascular disease. The disclosure also relates to hollow, high aspect ratio paclitaxel crystals.

BACKGROUND OF THE DISCLOSURE

Vascular diseases, such as arthrosclerosis, artery occlusion, and restenosis, are a leading cause of human mortality and morbidity. Vascular diseases arise from a variety of causes, and in some cases, necessitate surgical or endovascular intervention. Trauma to the vascular system can also necessitate surgical intervention to treat the traumatized anatomy. A common treatment for vascular disease is the short-term or long-term contact of a tissue with an endovascular medical device, such as a balloon or a stent, respectively, that is coated with a drug that prevents or reduces vascular disease at the site of contact. Upon contact of the endovascular medical device with a diseased vascular tissue, the drug elutes from the endovascular medical device into the surrounding tissue at the site of contact, thereby treating the vascular disease at a local, rather than systemic, level. The long-term contact, e.g., implantation, of endovascular medical devices including vascular grafts, stent-grafts, and stents, and the short-term contact of vascular medical devices including catheter-based balloons, are often undertaken to treat vascular diseases and vascular trauma.

Additional vascular diseases or vascular trauma that can require surgical or endovascular intervention include, but are not limited to, vascular injury, vascular prophylactic intervention, phlebitis, intimal hyperplasia, vulnerable plaques, carotid plaques, coronary plaque, vascular plaque, peripheral plaque, aneurismal disease, vascular dissections, atherosclerotic plaques, atherosclerotic lesions, vascular infection, stenosis, restenosis, and vascular sepsis.

The treatment of vascular disease at a local, rather than systemic, level is often preferred. Systemic administration of drugs can produce unwanted side effects, when compared to the local administration of a drug to a target tissue to treat vascular disease. The utilization of a drug-coated endovascular medical device has become a standard technique in the treatment of vascular disease.

Drug eluting balloons (DEBs) are one example of a drug-coated endovascular medical device. The literature discloses the use of DEBs for the treatment of vascular diseases, including coronary artery disease and peripheral artery disease (see e.g., U.S. Pat. No. 5,102,402, issued to Dror et al.). Dror et al. disclose placing a DEB in a blood vessel lumen to treat the vessel wall, inflating the balloon, and contacting the balloon surface with the luminal vessel wall to deliver a drug into the blood vessel wall. The dosing of the drug to the treatment site using DEBs can be highly variable and unpredictable immediately after implantation, and local drug levels in the vascular tissue can be highly variable and unpredictable over an extended time. It is therefore desirable to have improved implantable medical devices and methods for treating vascular disease that are reliable and reproducible in drug dosing.

Drugs that are used to treat vascular disease include antiproliferative, antiplatelet, or anticoagulant drugs. One example of an antiproliferative drug for the treatment of vascular disease, via its elution from a coated endovascular medical device, is paclitaxel.

Paclitaxel is a small molecule originally isolated from the needles and bark of the Pacific Yew tree (*Taxus brevifolia*). Paclitaxel has proven particularly successful for the treatment of vascular disease via its release from a coated endovascular medical device. Paclitaxel's role in the treatment of vascular disease is due to its ability to bind and stabilize cellular microtubules, thus preventing the migration, mitosis, and hyperproliferation of vascular smooth muscle cells, fibroblasts, and circulating immune cells.

Paclitaxel and other drugs for the treatment of vascular disease present several issues when used for coating endovascular medical devices, and when used for local release from the coated endovascular medical device to a surrounding tissue. Paclitaxel is only sparingly soluble in water or biological fluids such as blood, and it has a relatively narrow therapeutic window. Thus, while paclitaxel-eluting endovascular medical devices are used for the treatment of vascular disease, they are not completely effective due to a lack of coating robustness and drug elution considerations.

For example, the drug must first of all, be eluted from the coated endovascular medical device into the surrounding tissue during the contact time, whether it be short-term or long-term contact. The eluted drug must be transferred to the cells lining the diseased vessel, rather than be washed away by flowing blood. Finally, the drug must be available to the cells for a sufficient length of time, and at an appropriate concentration range, to exert its pharmacological effects while minimizing its side effects. Also, the drug coating must meet certain manufacturing and clinical needs to be an effective and commercially viable treatment for vascular disease. The polymorph form of paclitaxel, along with substrate characteristics, can influence the degree of coating robustness and the drug elution characteristics.

Paclitaxel is known to exist as several crystalline polymorphs and solvate or hydrate polymorphs (i.e., a crystal form with stoichiometric or non-stoichiometric amounts of solvent or water); the most studied being an amorphous form, an anhydrous crystalline form, and a dihydrate crystalline form. All three polymorphs have found use as coatings on medical devices for the local treatment of vascular disease. These polymorphs have numerous physical shapes, known in the art as a habit, including needles, plates, columns, irregular particles, spheres, etc. The ability of paclitaxel to dissolve (i.e., enter dissolution) in an aqueous or biological fluid is dependent upon the polymorph and the habit, as is its bioavailability and mechanical properties. The preparation and physical structure of various paclitaxel polymorphs have been previously described (for example, S H Pyo, Drying Technology, 25, 1759, 2007; J W Yoon, Korean J Chem Eng, 28, 1918, 2011; U.S. Pat. No. 6,858,644 to Benigni et al.).

Paclitaxel in its amorphous polymorph can be characterized by a lack of crystallinity, as measured by differential scanning calorimetry (DSC), X-ray diffraction (XRD), and other techniques known to the art. Amorphous paclitaxel can be prepared, inter alia, by solvent evaporation from solutions comprising low- or non-polar solvents such as dichloromethane (for example, Yoon, op. cit.; J H Lee, Bull Korean Chem Soc, 22, 925, 2001) The art describes amorphous paclitaxel typically taking the form of glasses, irregular fine particles, or grape-like particles. Amorphous paclitaxel is most soluble in organic pharmaceutical solvents and oils, such as polyglycols comprising poloxamer, for use as a liquid formulation.

Paclitaxel in its anhydrous crystalline polymorph is characterized by a melting temperature of about 223° C. as measured by DSC. Anhydrous crystalline paclitaxel can be prepared, inter alia, by precipitation from an organic solvent such as acetone, into a miscible organic nonsolvent such as ethyl acetate. Anhydrous crystalline paclitaxel further can be prepared, inter alia, by recrystallization from a polar organic solvent such as alcohol, acetone, or acetonitrile. Anhydrous crystalline paclitaxel has a unique XRD spectrum and a unique FTIR spectrum.

Paclitaxel in its dihydrate crystalline polymorph is characterized by a loss of water upon heating to as measured by thermal gravimetric analysis, and by various endothermic peaks at 70-140° C. as measured by DSC. Dihydrate crystalline paclitaxel can be prepared, inter alia, by precipitation from an organic, water miscible solvent such as acetone, into aqueous nonsolvent such as water. Dihydrate crystalline paclitaxel has a unique XRD spectrum and a unique FTIR spectrum, distinct from the anhydrous polymorph. The typical habit of dihydrate crystalline paclitaxel is regular needle-(acicular) shaped aggregates and regular plate-shaped aggregates. Dihydrate crystalline paclitaxel typically has the least apparent solubility in aqueous media of the three polymorphs.

Several references briefly discussed below describe various uses of paclitaxel in combination with endovascular medical devices.

Paclitaxel has been coated into the microstructure of endovascular medical devices, such as vascular grafts comprising porous ePTFE, using a solvent evaporation process (B. H. Lee, "Paclitaxel-coated expanded polytetrafluoroethylene haemodialysis graft inhibit neointimal hyperplasia in porcine model of graft stenosis," Nephrol Dial Transplant, 21, 2432, 2006). As described in the Lee reference, paclitaxel was loaded onto ePTFE vascular grafts using a dipping method. Briefly, dry paclitaxel was dissolved in acetone at 2 mg/ml or 10 mg/ml, and ePTFE vascular grafts were dipped vertically into these solutions and incubated for 30 minutes at 37° C. The paclitaxel loaded ePTFE vascular grafts were then dried and maintained under vacuum overnight to completely remove the solvent. No teachings were given on a paclitaxel crystal high aspect ratio habit adherent to the vascular graft, nor how to facilitate projection or extension of a paclitaxel crystal high aspect ratio habit from or into the ePTFE vascular graft. For example, see Example 12 infra and shown by FIG. 12A infra, wherein the acetone solvent yielded a smooth, glassy coating in an example of the instant disclosure.

U.S. Patent Publication No. 2010/0268321 to McDermott et al. teaches implantable medical device having a porous polymer (e.g., ePTFE, etc.) and crystals formed inside the pores of the porous polymer. The crystals can be paclitaxel. However, no teachings were given to a drug crystal high aspect ratio habit embedded within the porous polymer or the medical device, nor how to facilitate projection of a drug crystal high aspect ratio habit with respect to the substrate.

U.S. Pat. No. 6,827,737 to Hill et al. teaches an implantable composite device that is a multi-layered tubular structure which is particularly suited for use as an endoprosthesis or vascular graft. The prosthesis includes at least one extruded polytetrafluoroethylene (PTFE) tube. Furthermore, the prosthesis includes a second tube of a polymeric material designed to regulate delivery of a drug associated with the prosthesis to the site of implantation. The drug may be encapsulated within the polymer. The drug can be paclitaxel. No teachings were given on a drug crystal having a high aspect ratio habit projecting from a porous polymer or a medical device, nor extending at least partially into a porous polymer or a medical device.

U.S. Patent Publication No. 2011/0015664 to Kangas et al. teaches a drug-eluting balloon wherein paclitaxel is coated in an amorphous form onto a balloon surface comprising the polymer Pebax®, and then the amorphous paclitaxel is converted to a desired crystalline form in an annealing step that grows the crystalline drug in the coating in-situ on the balloon. Vapor annealing of a continuous integral amorphous paclitaxel coating results in solid state (or semi-solid) crystallization of the drug leading to crystalline coatings with the crystals oriented parallel to the balloon surface and robust crystal packing. As a point of contrast, this reference also shows an image of a cross-section of a prior art balloon in a folded configuration that shows small rod-like crystals in the fold area, but they show very poor association with the surface and seem to have grown to loosely fill void space under the balloon folds, with many crystals extending outward from, rather than parallel to, the surface. No teachings were given on a drug crystal high aspect ratio habit that projects from a porous polymer, nor a drug crystal high aspect ratio habit that extends into a porous polymer.

U.S. Patent Publication No. 2010/0272773 to Kangas et al. teaches a process for a medical device, an angioplasty balloon, having a drug coating thereon, wherein the drug has a plurality of characteristic morphological forms, wherein the process is controlled to produce a predetermined ratio of said morphological forms on the device. The sample from 20/80 THF/EtOH shows well formed fan-like paclitaxel crystals covering the balloon. The sample from 40/60 THF/EtOH shows discrete rod-like crystals. The annealing process is effective at converting the DEB coating from amorphous paclitaxel to crystalline form. No teachings were given on a drug crystal high aspect ratio habit that projects from a porous polymer, or a drug crystal high aspect ratio habit that extends into a porous polymer.

Many endovascular treatments require a sufficient amount of adhesion of the drug particle to the device substrate to withstand manufacturing and delivery, but also be readily detached from the device substrate upon contact with the treatment site to the tissue surface. Thus, a drug coating with improved robustness and adequate attachment to remain mostly intact during the handling and manipulations of manufacturing and during the medical procedures but detached upon tissue contact would be beneficial. In addition, such drug coatings that also reduce drug degradation or epimerization would also be beneficial.

SUMMARY OF THE DISCLOSURE

The present disclosure is directed toward composite materials comprising high aspect ratio habits of drug crystals which can be partially or fully extending into a substrate, and additionally, can be projecting from a substrate at an angle of about 20° to about 90°. The present disclosure is directed toward medical devices, such as medical balloons, comprising said composite. Said composite can be robust and provide improved attachment during manufacturing and during use of the device. The described composite can be used for the local treatment of vascular disease. The present disclosure is also directed toward paclitaxel crystals with a hollow acicular habit.

In accordance with one aspect of the disclosure, a composite material can comprise a plurality of high aspect ratio paclitaxel crystals extending at least partially into said porous substrate and optionally projecting from a porous substrate at an angle of at least 20 to 90 degrees relative to the substrate. In various embodiments, the substrate is a polymeric substrate. In various embodiments, the substrate comprises a porous microstructure, which can optionally comprise interconnected fibrils or nodes interconnected by fibrils. In various embodiments, at least a few of the plurality of paclitaxel crystals can define a lumen extending along the length of a paclitaxel crystal. In various embodiments, the few of the plurality of paclitaxel crystals can contain a second material located in the lumen. In various embodiments, the second material is at least one of less soluble or more soluble in an aqueous environment than the paclitaxel crystals. In various embodiments, the lumen can be sealed. In various embodiments, the plurality of paclitaxel crystals can be acicular. In various embodiments, the high aspect ratio crystals can have a ratio such that a major dimension is at least four times the minor dimension. In various embodiments, the substrate comprises a plurality of discrete crystals. In various embodiments, the substrate comprises a plurality of crystal aggregates. In various embodiments, the substrate comprises ePTFE. In various embodiments, the ePTFE can be coated with at least one of PVA, PEI, and PVP. In various embodiments, the substrate can be modified by at least one of plasma treatment, corona treatment, and surfactant treatment. In various embodiments, a majority of the plurality of paclitaxel high aspect ratio crystals comprise a flat tip. In various embodiments, a majority of the plurality of paclitaxel high aspect ratio crystals comprise a jagged tip.

In accordance with another aspect of the disclosure, a method of preparing a composite comprising a porous substrate and a drug crystal of high aspect ratio habit, such that the crystals are at least partially extending into the substrate and are projected from substrate at an angle of about 20 to 90 degrees with respect to the substrate and comprising the steps of preparing a solution of drug in the organic solvent, wherein the organic solvent is capable of wetting the substrate; applying the solution to the porous substrate; and causing the solvent to evaporate to form the drug crystal. In various embodiments, the substrate can comprise a node and fibril microstructure or microstructure of interconnected fibrils. In various embodiments, the substrate can comprise ePTFE. In various embodiments, the drug can comprise paclitaxel. In various embodiments, the drug crystal can be a hollow, acicular crystal. In various embodiments, the organic solvent comprises methanol. In various embodiments, the method can further comprise the step of treating the composite with at least one of solvent annealing, vapor annealing, and thermal annealing. In various embodiments, applying the solution can comprise at least one of pipetting, dipping and spraying. In various embodiments, the method can further comprise the step of applying a non-solvent, wherein the non-solvent comprises at least one of water, and ethyl acetate. In various embodiments, the porous substrate can form a surface of a medical device. In various embodiments, the medical device can be a catheter-based device.

In accordance with another aspect of the disclosure, a method of treating a disease locally can comprise the steps of radially expanding medical device from a first diameter to a second diameter, wherein the medical device comprises a substrate and the substrate contacts a tissue upon expansion, wherein the substrate comprises a polymeric substrate comprising a plurality of high aspect ratio paclitaxel crystals that at least partially extend into the substrate and can at least partially project from the substrate at an angle of at least 20 to 90 degrees relative to the substrate. In various embodiments, the substrate can comprise an excipient located thereon or within. In various embodiments, at least a portion of the plurality of high aspect ratio paclitaxel crystal can penetrate the tissue.

In accordance with another aspect of the disclosure, a drug crystal can comprise paclitaxel having a hollow crystal habit. In various embodiments, the hollow crystal habit is acicular. In various embodiments, the hollow crystal habit can be at least partially filled with another material. In various embodiments, the drug crystal is located on the surface of a medical device.

In accordance with another aspect of the disclosure, a composite material can comprise a substrate comprising a porous microstructure and an amount of crystalline paclitaxel comprising hollow crystal habits associated with the substrate. In various embodiments, the hollow crystal habits can be acicular. In various embodiments, the few of the plurality of paclitaxel crystals can contain a second material located in the lumen. In various embodiments, the second material is at least one of less soluble or more soluble in an aqueous environment than the paclitaxel crystals. In various embodiments, the lumen can be sealed. In various embodiments, the substrate can be polymeric. In various embodiments, the porous microstructure comprises interconnected fibrils or nodes interconnected by fibrils. In various embodiments, the substrate can be expanded polytetrafluoroethylene.

In accordance with another aspect of the disclosure, a method of making a drug delivery device having a substrate can comprise applying a solution comprising paclitaxel and an organic solvent to the substrate; allowing paclitaxel to crystallize through evaporation of the solvent, wherein the substrate comprises a polymer having a node and fibril microstructure or a microstructure of interconnected fibrils and wherein the organic solvent is capable of wetting the microstructure. In various embodiments, the polymer can comprise ePTFE. In various embodiments, the organic solvent can comprise at least one of methanol and ethanol.

In accordance with another aspect of the disclosure, a method of making a drug delivery device having a substrate can comprise the steps of applying a solution comprising paclitaxel to a substrate; causing the paclitaxel to crystallize; and exposing the paclitaxel to a vapor phase solvent to cause the paclitaxel to form acicular crystal habits that project from the surface at an angle of between 20 to 90 degrees. In various embodiments, the vapor phase solvent can comprise at least one of acetonitrile, methanol, and ethanol.

In accordance with another aspect of the disclosure, a medical device comprising an outer surface having a porous substrate and a plurality of high aspect ratio drug crystals, such as paclitaxel crystals, extending at least partially into said porous substrate, wherein the medical device comprises a first diameter and a second, diameter and the substrate is adapted to contact a tissue upon expansion to the second diameter. In various embodiments, the plurality of high aspect ratio crystals can project from the porous substrate at an angle of at least 20 to 90 degrees relative to the substrate. In various embodiments, at the first diameter, at least a portion of the plurality of high aspect ratio crystals do not project beyond to substrate, and optionally, at the second diameter, at least a portion of the plurality of high aspect ratio crystals can project from the porous substrate at an angle of at least 20 to 90 degrees relative to the substrate. In various embodiments, the porous substrate has a first thickness at a first diameter and a second thickness at a second diameter, wherein the first thickness is greater than the second thickness. In various embodiments, the medical device comprises an angioplasty balloon. In various embodiments, the porous substrate can comprise interconnected fibrils or nodes interconnected by fibrils. In various embodiments, the porous substrate can comprise an expanded fluoropolymer. In various embodiments, the porous substrate can comprise expanded polytetrafluoroethylene. In various embodiments, the expanded polytetrafluoroethylene has been plasma treated to create densified regions on the outermost surface.

BRIEF DESCRIPTION OF THE DRAWINGS

The features and advantages of the present disclosure will become more apparent from the detailed description set forth below when taken in conjunction with the drawings, wherein.

DETAILED DESCRIPTION OF THE DISCLOSURE

Figure 1:
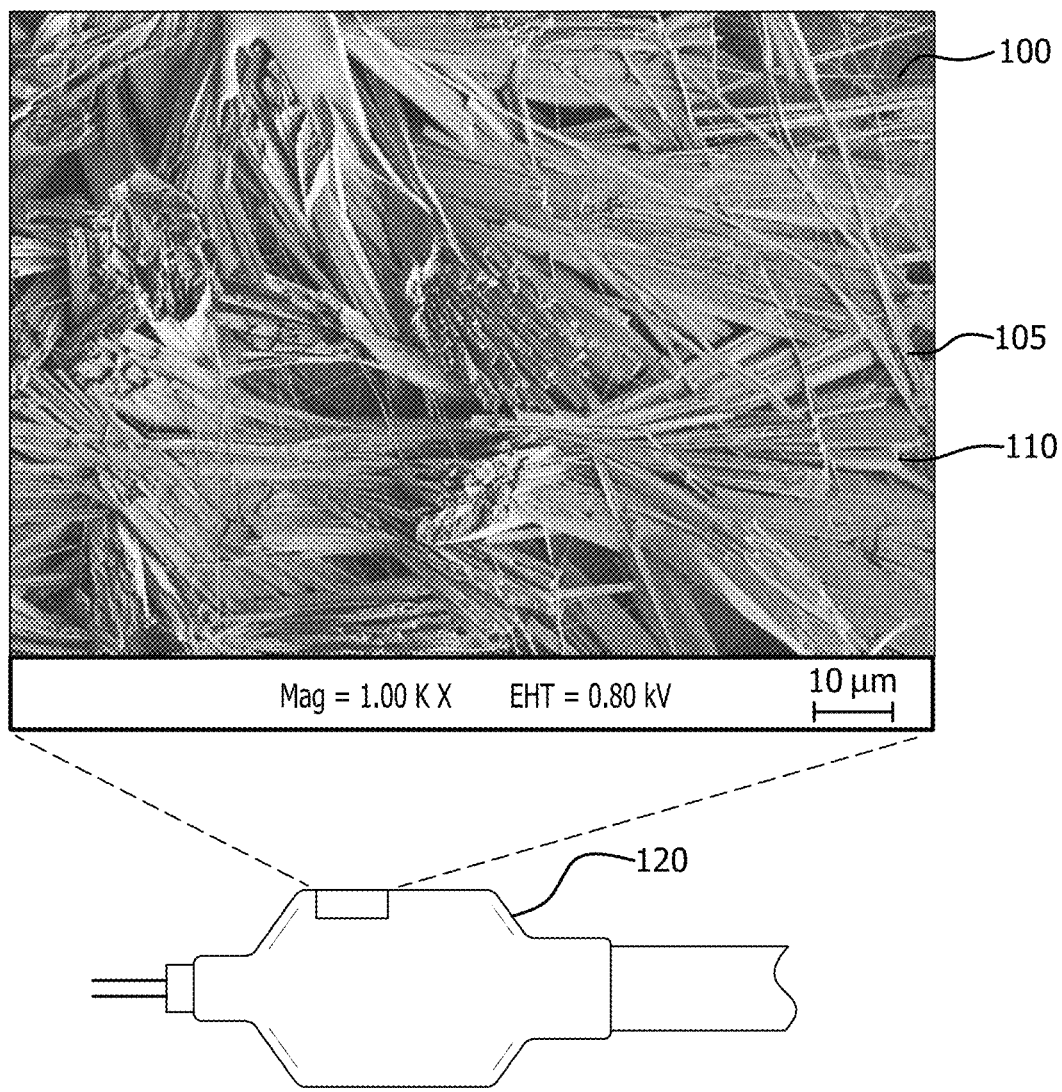
FIG. 1 is a schematic of a balloon device having a porous substrate on its outer surface and an SEM micrograph showing crystalline paclitaxel aggregates coated from methanol solvent onto the porous substrate comprising ePTFE of a microstructure comprising very highly elongated nodes interconnected by fibrils.

Persons skilled in the art will readily appreciate that various aspects of the present disclosure can be realized by any number of methods and apparatuses configured to form the intended functions. Stated differently, other methods and apparatuses can be incorporated herein to perform the intended functions. It should also be noted that the accompanying drawing figures referred to herein are not all drawn to scale, but may be exaggerated to illustrate various aspects of the present disclosure, and in that regard, the drawing figures should not be construed as limiting. Finally, although the present disclosure may be described in connection with various principles and beliefs, the present disclosure should not be bound by theory.

The disclosure relates to composites comprising substrates comprising drug crystals of high aspect ratio habit which project from a substrate and extend (embed?) at least partially into the porous substrate, as well as their methods of preparation and their methods of use, e.g., in the treatment of vascular disease. The present disclosure furthermore relates to methods of treating or preventing a vascular disease with a composite comprising a porous substrate and drug crystals of high aspect ratio habit projecting from the porous substrate, as well as their methods of preparation and their methods of use in the treatment of vascular disease. Said high aspect ratio crystals can be paclitaxel, which can be in solid or hollow form. Lastly, the disclosure is also directed toward hollow, acicular habits of paclitaxel, as well as the methods of use and preparations thereof.

A "habit" of a crystal describes its visible external shape. It can apply to an individual, discrete crystal, or to an aggregate of crystals. It can apply to a crystal visualized by any of a number of means, including but not limited to the naked eye, optical microscopy, electron microscopy, and nanoindentation.

A "high aspect ratio" habit is a crystal habit that has a major dimension length and a minor dimension length, such that the major dimension length is about at least four (4) times longer than the minor dimension length.

A "polymorph" is a material's molecular crystalline structure existing as two or more forms. Polymorphs can be the result of hydration, solvation, and unique molecular packing. The different forms of a material's amorphous molecular structure (i.e., there is no long-range ordering of the molecules) can also be considered a polymorph.

"Acicular" is a habit characterized by an elongated, slender, needle-like or column-like structure. It can apply to an individual, discrete crystal, or to an aggregate of crystals. An acicular crystal has a high aspect ratio. An acicular crystal can be solid or hollow. When referred to as hollow, an acicular crystal habit has a lumen that extends longitudinally into at least a portion of the crystal.

A "therapeutic agent" as used herein, which is used interchangeably with the term "drug", is an agent that induces a therapeutic or bioactive response in a cell, a tissue, an organ, or an organism including mammals or that aids in detection or some other a diagnostic procedure.

The term "medical device" includes, but is not limited to, a medical balloon (e.g., an angioplasty balloon), a stent, a stent graft, a graft, heart valve, heart valve frame or prestent, occluder, sensor, marker, closure device, filter, embolic protection device, anchor, cardiac or neurostimulation lead, gastrointestinal sleeves, and the like.

The term "vascular disease" includes, but is not limited to, vascular injury, vascular trauma, vascular prophylactic intervention, intimal hyperplasia, phlebitis, vulnerable plaque, carotid plaque, coronary plaque, peripheral plaque, vascular plaque, aneurismal disease, vascular dissection, atherosclerotic plaque, atherosclerotic lesion, vascular infection, vascular inflammation, stenosis, restenosis, and vascular sepsis.

The term "adhesion" includes to stick or to engage with a surface, e.g., the luminal wall of a vessel.

The terms "penetration", "penetrating", "penetrate", and the like, are a type of adhesion wherein an object has entered into, passed through, embedded, or pierced the outermost plane of a surface of a substrate into the interior of the substrate.

The terms "project", "projecting", "projection" and the like, are an orientation of an object where the object extends beyond the outermost plane of the substrate.

The terms "projection angle", "angle of projection", and the like, are the geometric angle that a projecting object has relative to the outermost plane of the substrate surface.

Figure 2:
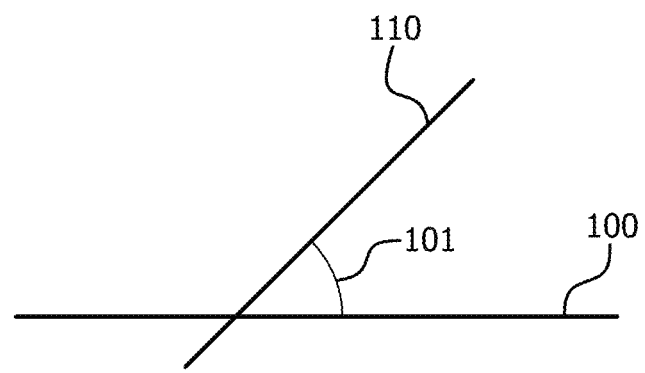
FIG. 2 is a schematic illustration of the angle of projection of a crystal relative to a substrate.
Figure 19A:
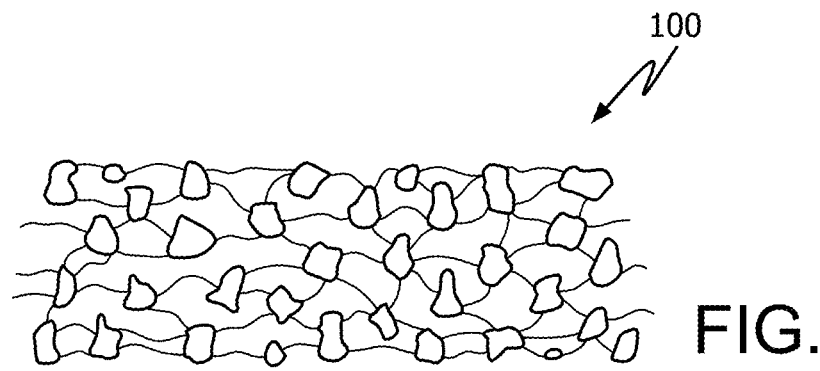
FIGS. 19A to 19D are schematics of a porous substrate comprising embedded drug crystals, wherein the porous substrate is compressible in its thickness dimension, and the embedded crystals are not compressible along their axes dimension, and wherein upon compression of the porous substrate in its thickness dimension the drug crystals project from the porous substrate.

In accordance with one aspect of the present disclosure, with reference to FIG. 1, a substrate 100 comprises a plurality of high aspect ratio crystals 110 comprising a therapeutic agent and projecting from the substrate 100 and optionally, extending into the substrate. The high aspect ratio crystals 110 can comprise an acicular habit and optionally a hollow acicular habit. The angle of projection 101 (see FIG. 2) relative to the substrate 100 can range from about 20 to 90 degrees. The plurality of crystals 110 can project from the substrate within the specified angle along a substantial portion of the section of coated substrate. Further, the plurality of crystals 110 can project from the substrate at an angle with respect to a flat section of substrate, i.e., a section that is not creased, folded, or wrinkled. In a further embodiment, the substrate 100 can comprise a porous microstructure (as in FIGS. 19A and 20A), and optionally, at least some of the high aspect ratio crystals 110 extend at least partially into the porous microstructure (as in FIG. 19B). The crystals 110 can be formed directly on the substrate 100. The angle of projection can be estimated or measured using a number of techniques, including but not limited to visualization using optical microscopy and SEM.

In forming directly on the substrate 100, the substrate 100 can comprise any suitable porous microstructure wherein the microstructure facilitates crystal formation that projects from, and optionally, at least partially extends into the substrate 100. In various embodiments, the porous microstructure comprises expanded fluoropolymer membranes. Non-limiting examples of expandable fluoropolymers include expanded PTFE, expanded modified PTFE, and expanded copolymers of PTFE. Patents have been filed on expandable blends of PTFE, expandable modified PTFE, and expanded copolymers of PTFE, such as, for example, U.S. Pat. No. 5,708,044 to Branca; U.S. Pat. No. 6,541,589 to Baillie; U.S. Pat. No. 7,531,611 to Sabol et al.; U.S. patent application Ser. No. 11/906,877 to Ford; and U.S. patent application Ser. No. 12/410,050 to Xu et al. The substrate 100 can also comprise a porous or fibrillated ultra-high molecular weight polyethylene (UHMWPE), a porous electrospun material and other porous polymers and metals.

The microstructure architecture can be varied to vary crystal properties, such as the habit type (e.g., clustered or discrete crystals, rod- or needle-like crystals, both solid and hollow), the dimensions (e.g., thickness, width, or aspect ratio), the geometry (e.g., hollow versus solid geometries), the orientation (e.g., projecting from the substrate) relative to the substrate, and the purity and perfection of the crystal. The porous microstructure can comprise nodes and fibrils, the size and spatial qualities of which can be varied. For example, in some embodiments, the microstructure can be highly fibrillated or have no distinguishable or very small nodes. In other embodiments, the microstructure can have large or elongated nodes. In yet other embodiments, the microstructure can have a node and fibril microstructure somewhere in between, e.g., a microstructure with intermediate-sized nodes. Additionally, the porosity or average pore size of the microstructure can create a tight microstructure or an open microstructure. "Tight" as used herein means that the spacing between the fibrils, nodes, or fibrils and nodes is smaller than the width of the exposed section of crystal. For example, in FIG. 13C, the crystals 110 are shown, and the width of the crystals 110 is much larger than the microstructure 100 on which they were formed. "Open" as used herein means that the spacing between the fibrils, nodes, or fibrils and nodes is larger than or equal to the width of a crystal. For example, in FIG. 1, the crystals 110 are shown passing through the spacing of the fibrils 105. Both microstructures allow for extension and/or embedding into the microstructure. Other porous microstructures that facilitate projections from, and optionally, at least partial extension and/or embedding of the crystal into the substrate, includes woven, knitted, felted, carded, spun, laser drilled, and/or neutron drilled materials or the like. Said porous microstructure can be further treated or coated to vary crystal formation, such as by plasma, corona, and/or surfactant treatment or coated with polyvinyl alcohol (PVA), polyethyleneimine (PEI), polyvinylpyrollidone (PVP), or other polymeric coatings. Said treatments and coatings may modify the surface energy of the substrate, or may modify the microstructure of the substrate. For example, the substrate may be modified for example by a combination of high energy processing followed by heating, to produce inter alia three dimensional microstructures on the substrate surface, such as those described in U.S. Pat. No. 7,736,739.

Similarly, the concentration levels of the therapeutic agent and/or solvent or blend of solvents (referred herein as a solvent system) from which the crystals form can be adjusted to adjust the habit (e.g., clustered or discrete crystals, rod- or needle-like crystals), the dimensions (e.g., thickness, width, or aspect ratio), the geometry (e.g., hollow versus solid geometries), the orientation relative to the substrate, and the purity and perfection of the crystal. The solvent system can comprise an organic solvent(s) and/or supercritical solvents, wherein the solvent has the ability to wet the substrate and has the ability to dissolve the therapeutic solvent. Optionally, the microporous substrate may be surface-treated to aid the wetting and imbibement of solvent containing dissolved therapeutic agent, or to aid the formation of crystals during crystallization.

For crystals grown by solvent evaporation under ambient conditions (about 25° C. and about 1 atm barometric pressure), the solvent system has a volatility and heat capacity to readily evaporate and induce super-saturation of the therapeutic agent. For example, a solvent system for solvent evaporation crystallization techniques can comprise methanol and/or ethanol. Methanol and/or ethanol as a primary solvent facilitate hollow acicular crystals under certain conditions. The solution concentration can be on the order of about 0.001 mg/ml to about 100 mg/ml.

A solvent system can comprise a solvent system additive(s) which can alter the dimension, habit, tip feature, and the like. For example, a solvent system can comprise methanol and urea. The ratio of the therapeutic agent to urea can range from 10:1 to 1:15 or more.

Also relevant to affecting the crystal properties is the manner of crystallization. High aspect ratio habits of crystals can be fully or partially adhered onto or into a porous substrate, such as ePTFE, using a variety of coating methods, including but not limited to solvent evaporation and vapor annealing. A method of crystallization can comprise at least one of solvent evaporation or vapor annealing. Using a solvent evaporation method, the drug is dissolved in an appropriate solvent and applied to the substrate, whereupon during and after evaporation of the solvent the drug crystallizes as a high aspect ratio habit that is fully or partially embedded, adhered, or otherwise coated onto the ePTFE. The solvent can be applied to the substrate with a variety of techniques including pipetting, dipping, spraying, brushing, and the like.

Using vapor annealing method, the drug is dissolved in an appropriate solvent, applied to the substrate, and the solvent evaporated, whereupon exposure to an appropriate solvent vapor the drug crystallizes as a high aspect ratio habit that is fully or partially embedded, adhered, or otherwise coated onto the porous ePTFE. Solvent systems for vapor annealing can comprise at least one of acetonitrile, methanol, tetrahydrofuran, chloroform, isopropyl alcohol, hexane, and ethanol.

Other techniques or post-crystallization treatments can include thermal annealing, quenching, vitrifying, vacuum, sonicating, and/or. Said techniques can be utilized to alter the habit type, dimensions, orientation, perfection, or purity. On the other hand, post-crystallization techniques can preserve or inconsequentially alter the habit type, dimension, orientation, perfection, and/or purity. For example, as described in Example 9, sterilizing the substrate with ethylene oxide did not consequentially impact the crystal properties.

Figure 3A:
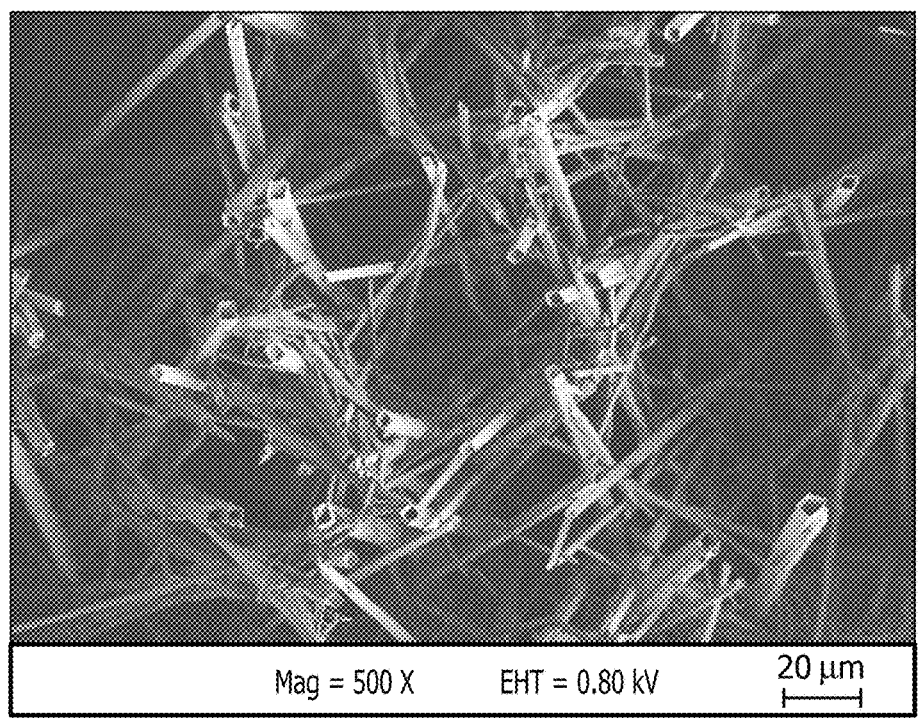
FIG. 3A is an SEM micrograph showing discrete hollow acicular paclitaxel crystals coated from methanol onto a porous substrate comprising ePTFE of a microstructure comprising very highly elongated fibrils.
Figure 11A:
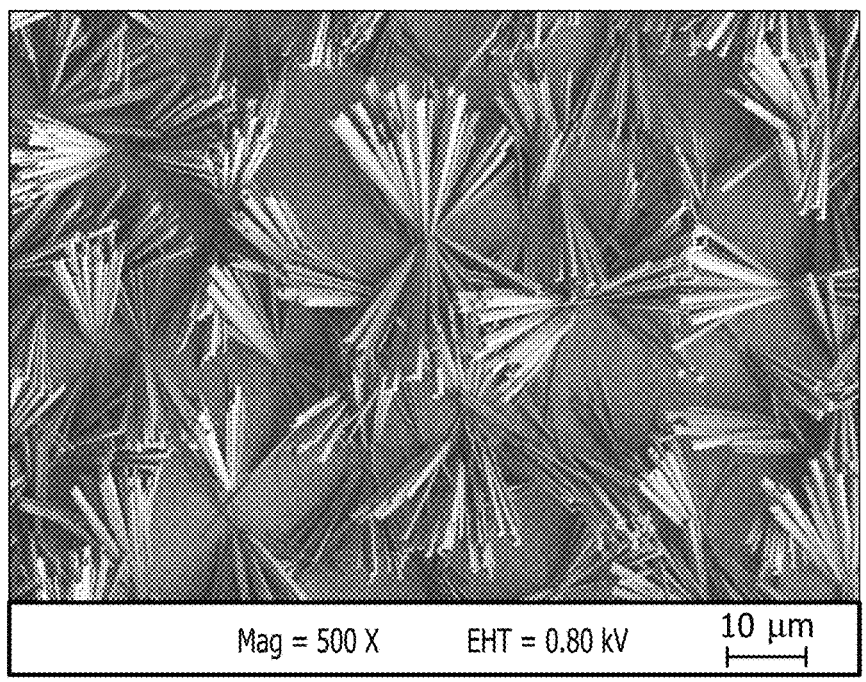
FIGS. 11A to 11D are SEM micrographs showing paclitaxel crystals of various habits coated from methanol solvent and various vapor annealing, onto a porous substrate comprising ePTFE of a microstructure comprising very highly elongated fibrils.

Crystal geometry, dimension, uniformity, perfection, or purity can facilitate adhesion and, optionally, penetration into a tissue. These factors can be controlled by varying the concentration of the solution, the type of substrate, the architecture of the substrate's microstructure, the type of solvent(s), the crystallization technique or processing, and the like. For example, the aspect ratio of a crystal can be adjusted to be 1:4 up to 1:50 or more. The shape of the end of the crystal can also be adjusted. For example, the tip 111 can be a generally flat tip (as shown, e.g., in FIGS. 1, 3A and 4 and FIGS. 11A to 11C) or a more pointed or jagged tip 111 (as shown, e.g., in FIGS. 14A, 14C, 14D, and 15C). These cited images are only provided as illustrative samples and are not the only images of flat, jagged, or pointed ends provided herein. Another variation includes coating a substrate with a plurality of discrete crystals 110 (as shown in FIG. 3A) or a plurality of crystal aggregates or clusters 112 (as shown in FIG. 11A).

In accordance with the present disclosure, with reference again to FIG. 1, a medical device 120 can comprise the high aspect ratio crystals 110 as described located on the surface 100 of a medical device and projecting from the surface 100. The medical device 120 can facilitate short-term contact with a tissue or long-term to permanent contact with a tissue. Contact less than 10 minutes is short-term contact and contact greater than 10 minutes is long-term contact. Said crystals 110 can comprise or consist of paclitaxel. Said crystals 110 can have an acicular habit and further a hollow acicular habit.

The crystals 110 can be pre-coated to a medical device 120 such as a vascular prosthesis, or a catheter-based device, such as a stent, stent graft, or balloon, prior to catheter insertion into a vascular structure. For example, the high aspect ratio crystals 110 can be coated to at least one portion or one surface of a medical device, vascular prosthesis, or catheter-based device including, but not limited to, a stent, stent graft, vascular graft, angioplasty balloon, microneedle studded balloon, and other vascular prosthesis. The coating can be continuous or discontinuous, covering at least a portion of the medical device. Furthermore, the crystals 110 of the coating can be partially or fully adhered onto (and optionally, extend or embed into) at least one surface of the medical device. In further embodiments, the crystals 110 of the coating can project from said at least one surface at a projection angle of about 20° to about 90°.

Figure 19B:
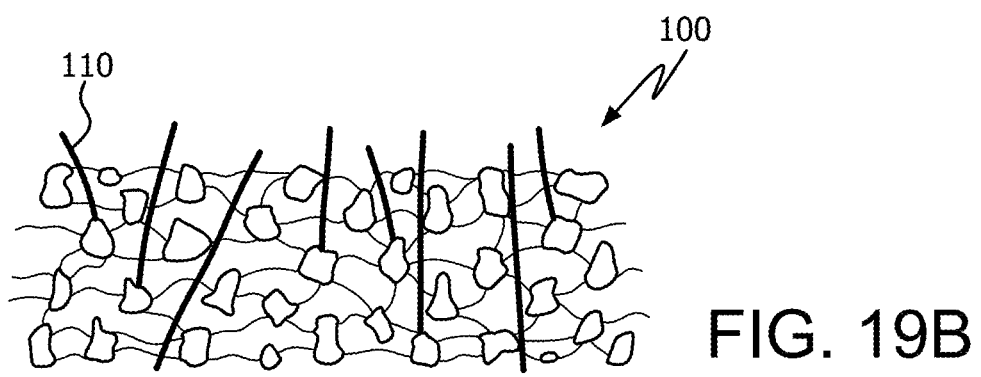
Figure 19C:
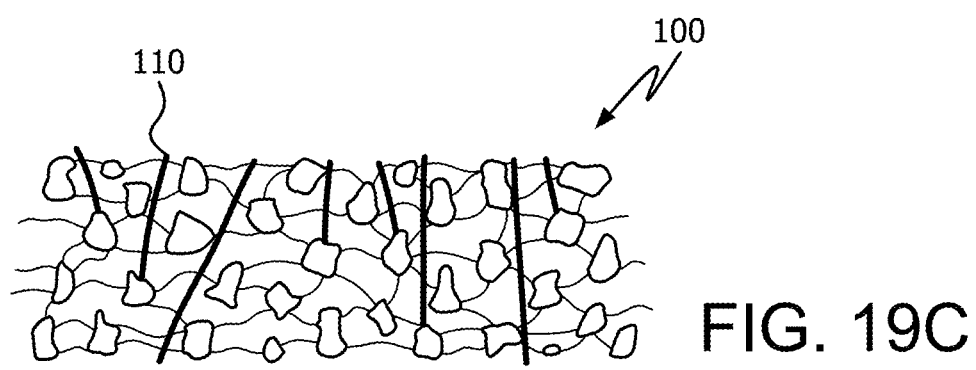
Figure 19D:
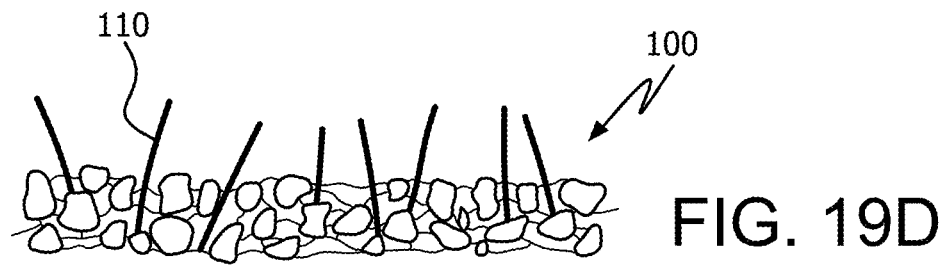
Figure 20A:
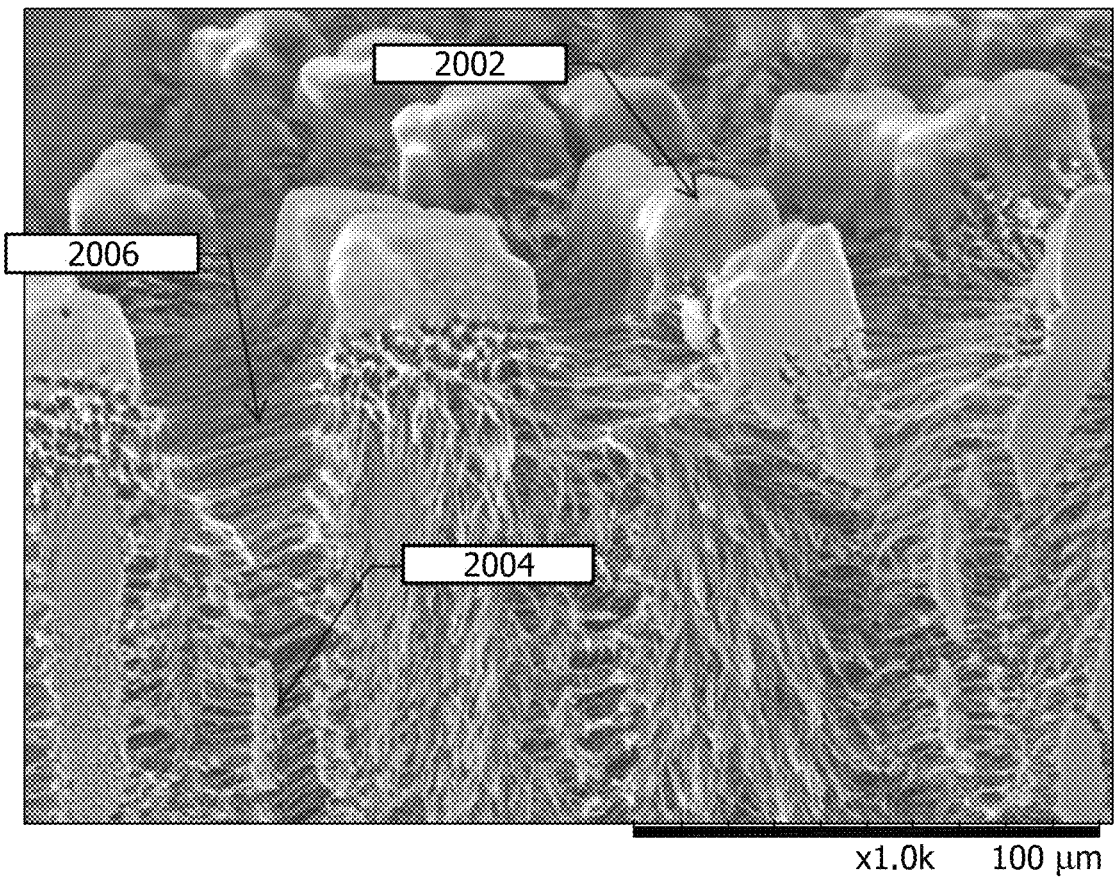
FIGS. 20A and 20B show SEM micrographs of a porous ePTFE microstructure comprising islands of PTFE or densified regions of ePTFE attached to and atop an underlying ePTFE microstructure, in cross section view and in plan view.
Figure 20B:
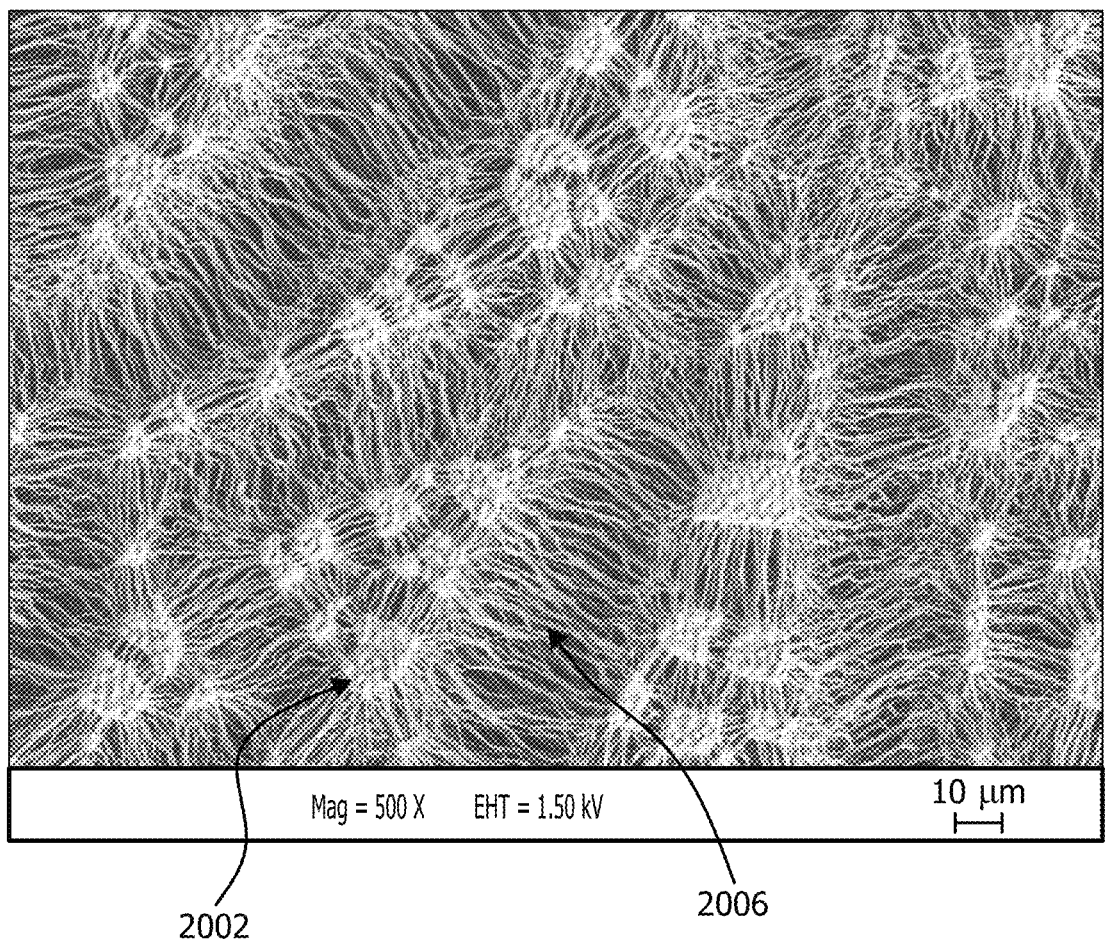

In another embodiment, the crystals are embedded in the microporous substrate and do not project from said at least one surface, as shown in FIGS. 19C and 20B. The crystals can be coated into the microporous substrate using techniques that prevent the projection of the crystals beyond the substrate outer surface. Alternatively, those portions of the crystals that project beyond said substrate outer surface (such as seen in FIG. 19B) may be planed off, using apparati known to the art including but not limited to planing knives, laser ablation, electrical current exposure, vapor exposure, solvent exposure, thermal exposure, mechanical abrasion, high energy processing such as plasma or corona, and the like. In this embodiment, the crystals that do not project beyond said substrate outer surface are effectively shielded against damage during manufacturing, storage, delivery to an anatomical site and initial device deployment. In a further embodiment, said effectively shielded crystals are capable during device implantation of projecting beyond the outer surface of said microporous substrate by causing compression along the thickness of the substrate. In this manner, the crystals can project from said outer surface at a projection angle of about 20° to about 90°, as shown in FIGS. 19D and 20C.

The coating on the medical device 120 comprising high aspect ratio habit crystals 110 that are not parallel to the surface 100 can facilitate a more robust adhesion to the substrate useful during manufacturing and during clinical procedures, as well as facilitate adhesion on or optionally penetration into a tissue or into the wall of a tissue. Said adhesion and optional penetration of individual particles of high aspect ratio habit crystals 110 can facilitate an improved transfer and/or retention of crystals 110 from the medical device 120 to the tissue at the site of contact, rather than be flushed from the site by flowing blood or other surgical techniques. The ability to create a particle coating with projecting crystals 110 can facilitate an improved delivery in terms of accuracy and reliability of dosing of the tissue during contact.

In accordance with the present disclosure, the high surface area, high vapor transmission rate, and relatively high thermal conductivity of ePTFE can facilitate drug solvation and mass transport, and provide for a steep thermal gradient, necessary for the growth of high aspect ratio habit crystals that are fully or partially extending into the microstructure. As is set forth in Example 8, such crystals show DSC thermal behaviors distinct from crystals that are adherent to, but that do not penetrate a non-porous substrate, including crystal melting and crystal perfection.

In accordance with the present disclosure, a therapeutic agent that is crystallized to form a high aspect ratio crystal on a porous substrate or extend at least partially into a substrate as described herein can comprise paclitaxel and its analogs. Other suitable therapeutic agents include rapamycin and its analogs. The therapeutic agents which can be used in embodiments of the present disclosure can be any therapeutic agent or substance that forms an acicular habit on a porous substrate or extends at least partially into a substrate.

Figure 10:
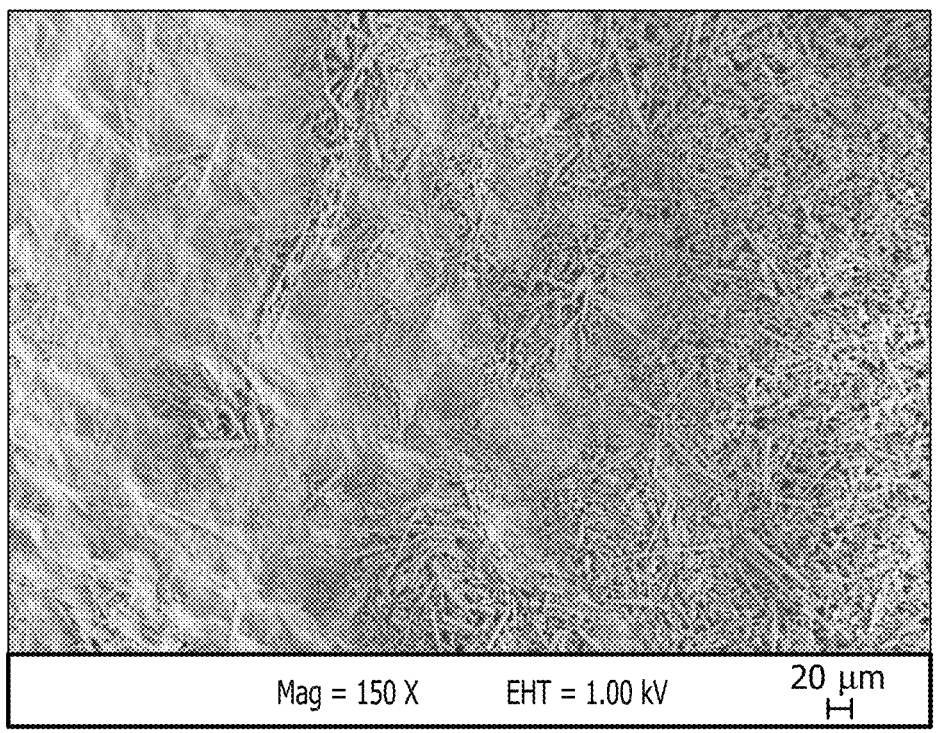
FIG. 10 is an SEM micrograph showing paclitaxel crystals engaged and embedded into a vascular tissue.

The described therapeutic agent coated on the described substrate is discontinuous on a microscopic scale, even though it can appear continuous on a visual scale. The crystals being at least partially extended into the microstructure are not continuous, as the nodes/fibrils break up the coating's continuity, as illustrated schematically in FIGS. 19B, 19C and 20B. Thus, during a sufficiently forceful contact with a tissue (e.g., a desired pressure of an inflated device in pressure contact with a tissue), the crystals can penetrate into the tissue as smaller, more uniform particle sizes, as is illustrated in FIG. 10, rather than as disperse, large, continuous sheets (shards, flakes, etc) of drug coating. The size of the particles can be controlled in the coating process to give a predictable size distribution during contact with the tissue.

In accordance with the present disclosure, the described substrates can be utilized in interventional techniques. Interventional techniques routinely involve minimally invasive procedures. Often this technique is initiated by a puncture or cut-down of a vascular structure and insertion of a catheter through an interventional access site into the vascular structure. Interventional access sites can include, but are not limited to, access through an implanted vascular prosthesis, brachial artery, carotid artery, iliac artery, femoral artery, aorta, and other arterial or venous sites.

After insertion of a catheter through an interventional access site into the vascular structure, the catheter can then be guided to a site with a vascular disease in need of vascular treatment (i.e., a vascular treatment site), from the interventional access site. The vascular treatment site can include, but is not limited to, vascular conduits such as a blood vessel, a vascular graft, a vascular stent, a vascular filter, a vascular anastomosis, and a vascular stent graft. In an interventional treatment, a medical device contacts a treatment site. Following a contact time sufficient for at least a portion of the high aspect ratio habit crystals of drug to adhere to a vascular treatment site to treat the vascular disease, the medical device can be optionally removed. The contact time can be short term, can be long term, or can be permanent.

By way of example, the high aspect ratio habit crystals of drug described herein can be pre-applied to or formed on at least one surface of a catheter-based device prior to catheter insertion into a vascular structure. For example, high aspect ratio habit crystals of drug can be coated to at least one surface of a catheter-based device including, but not limited to, a stent, stent graft, medical balloon (e.g., a angioplasty balloon or microneedle studded balloon), and other vascular prostheses. The coating can be continuous or discontinuous, covering at least a portion of the catheter-based device. The crystals of the coating are fully or partially adhered onto and optionally extended and/or embedded into at least one surface of the catheter-based device, as shown in FIG. 19B. In addition, said acicular crystals project against said at least one surface at a projection angle of about 20° to about 90°.

Catheter-based devices often have a first diameter and a first surface area prior to and during insertion of the catheter-based devices into a vascular tissue. After insertion into the vascular tissue, the catheter-based devices are mechanically expanded to a second diameter and a second surface area within the vascular structure. When the catheter-based medical device is mechanically expanded to the second diameter and second surface area, the projecting crystals on the at least one surface of the medical device adhere to the wall of the vascular tissue and optionally extend a portion of the crystals into the wall of the vascular tissue. The catheter-based medical device is optionally returned to the first diameter and first surface areas, thereby allowing its removal from the vascular tissue. The said projecting crystals that have adhered onto and optionally penetrated into the wall of the vascular tissue remain adhered onto and optionally penetrated into the wall of the vascular tissue during the return of the catheter-based medical device to the first diameter and first surface area, thereby treating the vascular disease.

In another embodiment of a catheter-based device having a first diameter and a first surface area prior to and during insertion of the catheter-based devices into a vascular tissue, the crystals do not project beyond the external surface of the device, as shown in FIGS. 19C and 20B. In this manner, the crystals are embedded within the microporous substrate, and are effectively encapsulated and mechanically protected from damage during manufacturing or storage, and from premature tissue exposure or particulation during device insertion into a vascular tissue and tracking to the target tissue. After insertion into the vascular tissue, the catheter-based devices are mechanically expanded to a second diameter and a second surface area within the vascular structure. When the catheter-based medical device is mechanically expanded to the second diameter and second surface area, the embedded crystals then project beyond the outer surface of the substrate at a projection angle of 20-90°, as shown in FIGS. 19D and 20C. The projecting crystals adhere to the wall of the vascular tissue and optionally penetrate a portion of the crystals into the wall of the vascular tissue. The catheter-based medical device is optionally returned to the first diameter and first surface areas, thereby allowing its removal from the vascular tissue. The said projecting crystals that have adhered onto and optionally penetrated into the wall of the vascular tissue remain adhered onto and optionally penetrated into the wall of the vascular tissue during the withdrawal of the catheter-based medical device from the vascular tissue. In various embodiments, when the catheter-based medical device is mechanically expanded to the second diameter and second surface area, a substrate can comprise nodes, fibrils, or nodes and fibrils. In a further embodiment, these nodes, fibrils, or nodes and fibrils can undergo a change in alignment during expansion to the second surface area thereby altering the orientation of the said embedded crystals. This can facilitate rotation of, extension of, or reorientation of the crystals so that they project beyond the outer surface of the substrate at a projection angle of 20-90°, as shown in FIGS. 19D and 20C.

Described composites can be utilized in surgical or interventional procedures, such as in catheter based vascular or non-vascular devices. In addition to vascular applications, the described composite can be used in relation to, gastro-intestinal, neural, cranial, ophthalmic, orthopedic, renal, hepatic, urinary, sinus treatments, and the like.

Figure 3B:
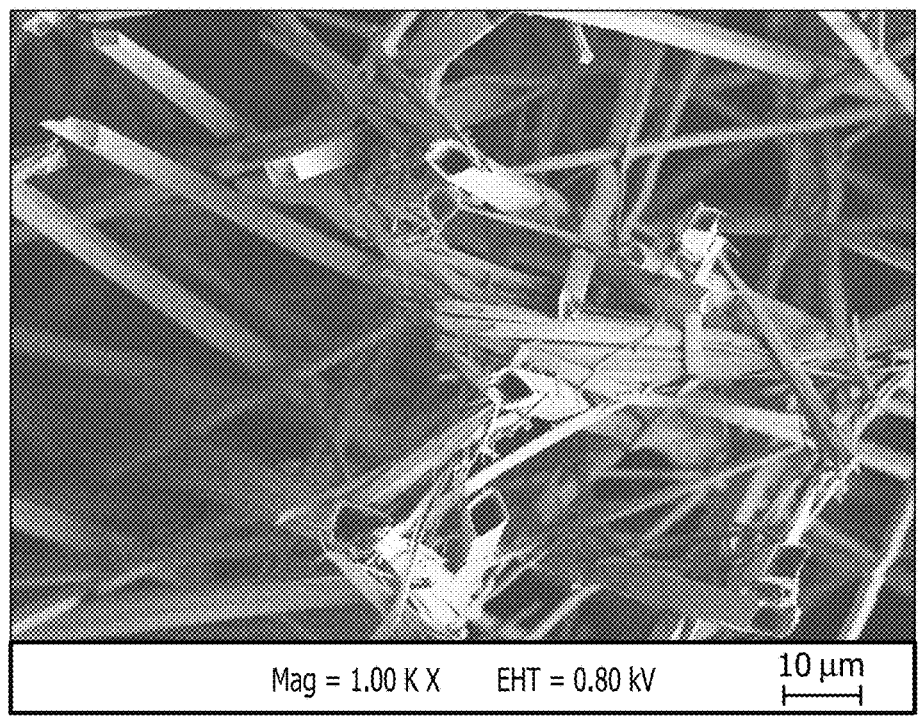
FIG. 3B is an SEM micrograph at a higher magnification showing discrete hollow acicular paclitaxel crystals coated from methanol onto a porous substrate comprising ePTFE of a first microstructure comprising very highly elongated fibrils.

In accordance with another aspect of the present disclosure, with reference to FIGS. 3A and 3B, the high aspect ratio habit crystals 110 can comprise hollow acicular paclitaxel, which can be used in a clinical treatment or formulation, such as for the treatment of cancer or vascular disease. Such treatments or formulations include the addition of the crystals to an oral form, a tablet form, a suspension, an emulsion, a parenteral form, an intravenous form, an enteral form, an injectable form, or other formulations. Such formulations may or may not include the need for a medical device. Such formulation may or may not include the addition of pharmaceutical vehicles, excipients, fillers, additives, nano- and micro-carriers, and the like. Such crystals can be removed from the substrate upon which it was formed for use in the described treatments and formulations.

In an embodiment, the lumen of the hollow crystals can be filled at least partially with a second material, such as a therapeutic agent, an excipient, an additive or a therapeutic agent and an excipient or additive. The therapeutic agent can have an equal degree of aqueous solubility than the paclitaxel hollow crystal or a greater or lesser amount of relative aqueous solubility. In addition, an end cap or seal of various materials can be placed on the tip of the hollow acicular crystal once filled.

The following examples describe the manner, process of making, and using the present disclosure and are intended to be illustrative rather than limiting.

EXAMPLES

Example 1

This example describes the preparation of a porous sample substrate comprising ePTFE of a first microstructure comprising very highly elongated fibrils.

An ePTFE membrane of approximately 0.0002" thickness was prepared as per U.S. Pat. No. 7,306,729 to Bacino et al., incorporated herein by reference in its entirety. A fluoropolymer adhesive comprising a thermoplastic copolymer of tetrafluoroethylene and perfluoromethyl vinyl ether was prepared generally in accordance with U.S. Pat. Nos. 7,049,380 and 7,462,675 to Chang et al., incorporated herein by reference in their entirety. The ePTFE membrane was cut to approximately 20 mm×50 mm, and was adhered to a glass slide (#48300-025, VWR). An adhesive solution was prepared by dissolving the fluoropolymer adhesive in solvent (Fluorinert FC-75, 3M) at a concentration of approximately 3%. A light coating of the adhesive solution was applied to the glass slide, and the ePTFE membrane was applied and smoothed to remove wrinkles and bubbles, then heated under slight pressure (approx 0.02 atm) at 60° C. in an oven for 24 hr to remove the solvent.

Example 2

This example describes the preparation of a porous sample substrate comprising ePTFE of a second microstructure comprising very highly elongated nodes interconnected by fibrils.

An ePTFE membrane of approximately 0.0007" thickness was prepared generally in accordance with U.S. Pat. No. 5,814,405 to Branca et al., incorporated herein by reference in its entirety. The ePTFE membrane was cut to approximately 20 mm×50 mm, and was adhered to a glass slide (#48300-025, VWR) as per Example 1.

Example 3

This example describes the preparation of a nonporous sample substrate comprising nylon.

Figure 5:
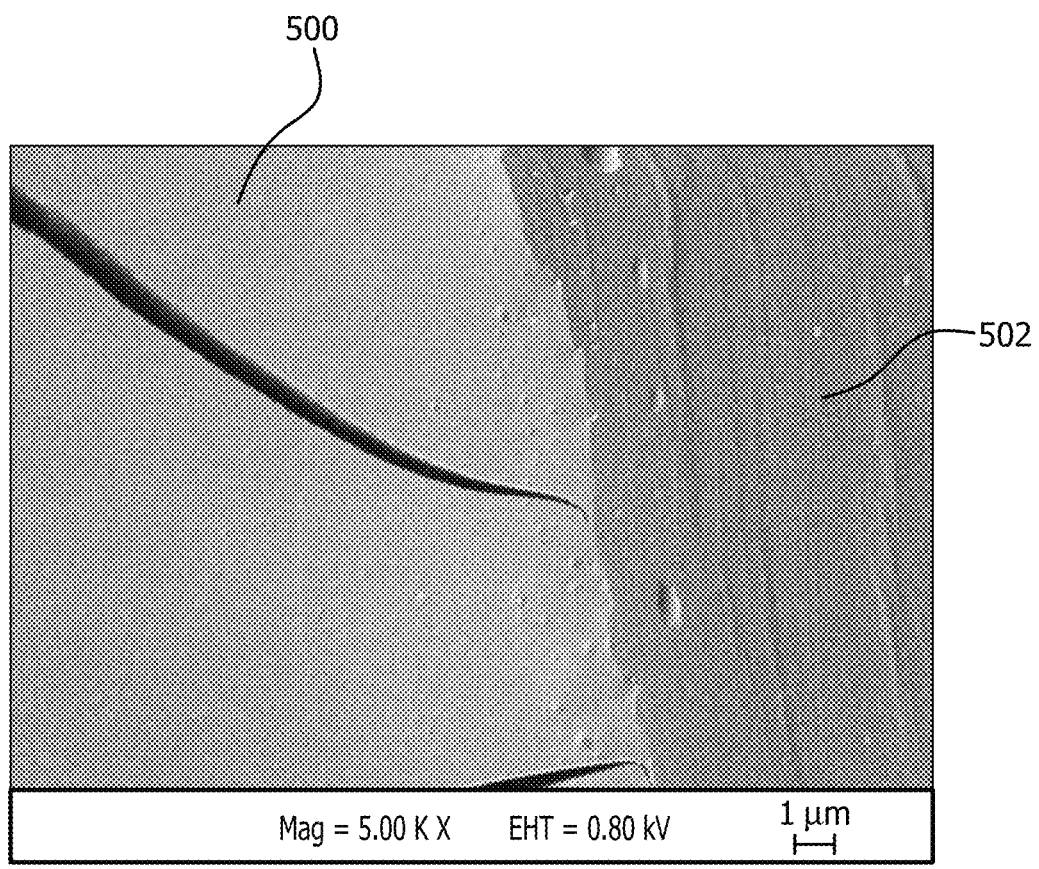
FIG. 5 is a scanning electron microscope (SEM) micrograph showing paclitaxel coated from acetonitrile solvent onto a nonporous substrate comprising nylon.

A nylon balloon (part number BMT-035, Bavaria Medizin Technologie, Munich Germany) was inflated with air to remove folds and pleats. A 20×50 mm film was cut from the balloon with a razor blade, and taped to a glass slide (#48300-025, VWR) using cellophane tape. The non-porous nature of this substrate is depicted in FIG. 5.

Example 4

This example describes the general procedure for the preparation of drug crystals onto a substrate using solvent evaporation.

Paclitaxel (LC Laboratories, Boston Mass.) was dissolved at room temperature by stirring into methanol (ACS grade, Aldrich), acetonitrile (ACS grade, Aldrich), acetone (ACS grade, Aldrich), or chloroform (reagent grade, Sigma), at a concentration of 10 to 30 mg/ml, optionally containing urea (reagent grade, Sigma) at a mass ratio of 1:1 to 8:1 (paclitaxel:urea). 50 to 500 µl of the paclitaxel solution was then cast onto the substrates of Examples 1 through 3, by depositing the solution from a pipettor over the surface area of the ePTFE or nylon substrates. The samples were air-dried in a laminar fume hood at about 20° C. at an ambient atmospheric pressure of about 773 mm Hg to cause the solvent to evaporate. (The paclitaxel solution can be applied to the substrate in a variety of ways including pipetting, dipping, spraying, brushing, and the like.)

Example 5

This example describes the SEM visualization and orientation of drug crystals adhered onto the substrates of Example 3 as coated according to Example 4.

Figure 6:
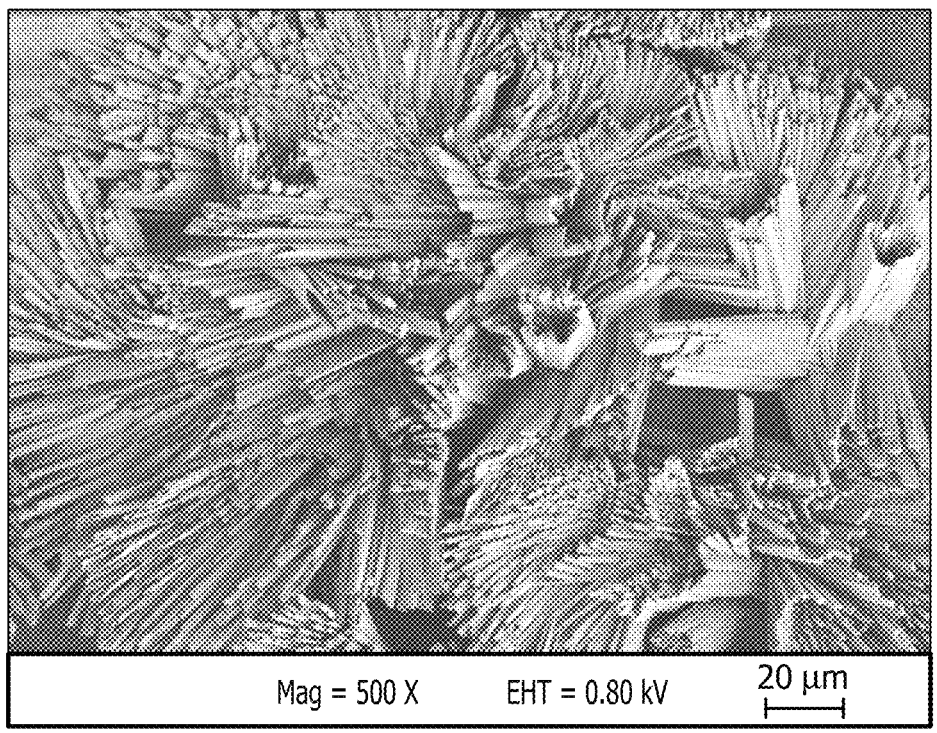
FIG. 6 is an SEM micrograph showing crystalline paclitaxel aggregates coated from methanol solvent onto a nonporous substrate comprising nylon.
Figure 7:
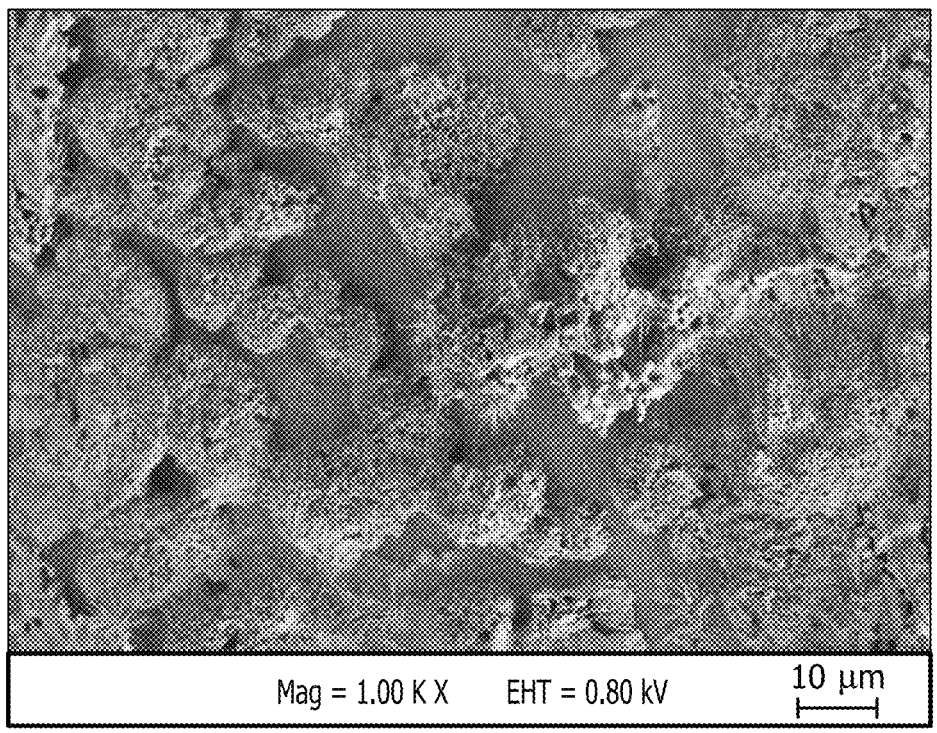
FIG. 7 is an SEM micrograph showing crystalline paclitaxel aggregates comprising a urea excipient coated onto a nonporous substrate comprising nylon.

As seen in FIG. 5, paclitaxel 500 coated onto nylon 502 from acetonitrile solvent (10 mg/ml) produced a smooth, continuous coating, absent of any high aspect ratio habits. As seen in FIG. 6, paclitaxel coated onto nylon from methanol solvent (10 mg/ml) produced a plurality of aggregates of paclitaxel crystals comprising high aspect ratio habits. The aggregates were observed to be adherent to the nylon substrate, but did not penetrate or otherwise embed into the bulk of the nylon substrate. Most of the aggregates were observed to project from the nylon substrate at a projection angle of about 20° to about 90° relative to the substrate. As seen in FIG. 7, paclitaxel comprising a urea excipient (1:1 mass ratio) coated onto nylon from methanol (10 mg/ml paclitaxel) produced a plurality of aggregates of paclitaxel/urea crystals comprising multiple habits including irregular shapes, "coral"-like shapes, whiskers, rods, and the like. The aggregates were observed to be adherent to the nylon substrate, but did not extend into the bulk of the nylon substrate. The aggregates did not show any orientation relative to the nylon substrate.

Example 6

This Example describes the SEM visualization and orientation of drug crystals embedded and oriented onto the substrates of Example 1 as coated according to Example 4.

Figure 4:
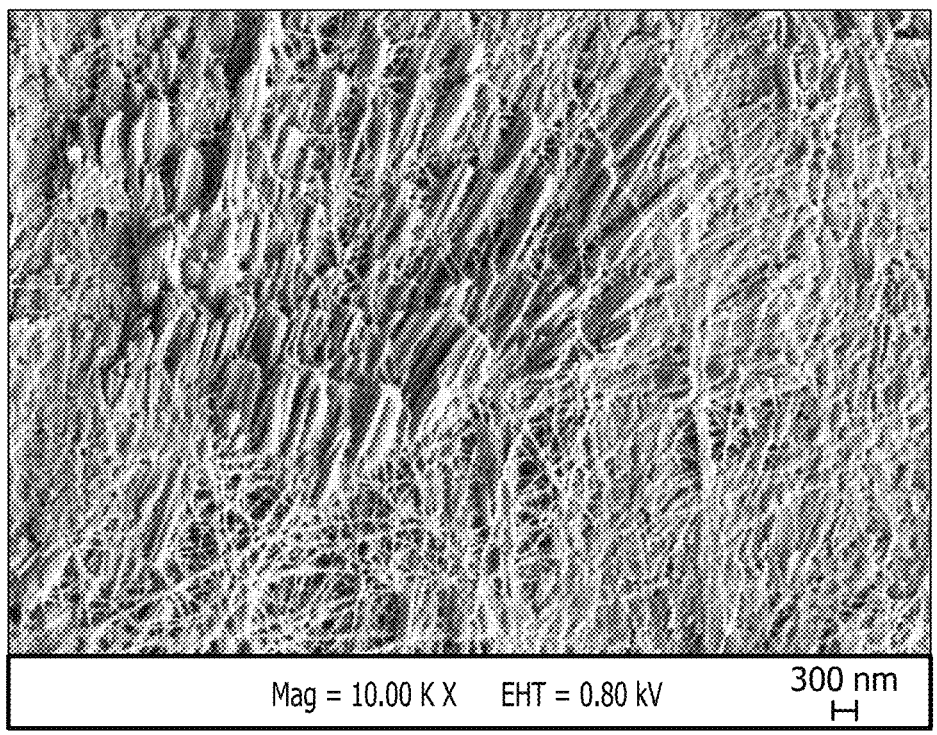
FIG. 4 is an SEM micrograph showing acicular paclitaxel crystal aggregates comprising a urea excipient coated onto a porous substrate comprising ePTFE of a first microstructure comprising very highly elongated fibrils.
Figure 8:
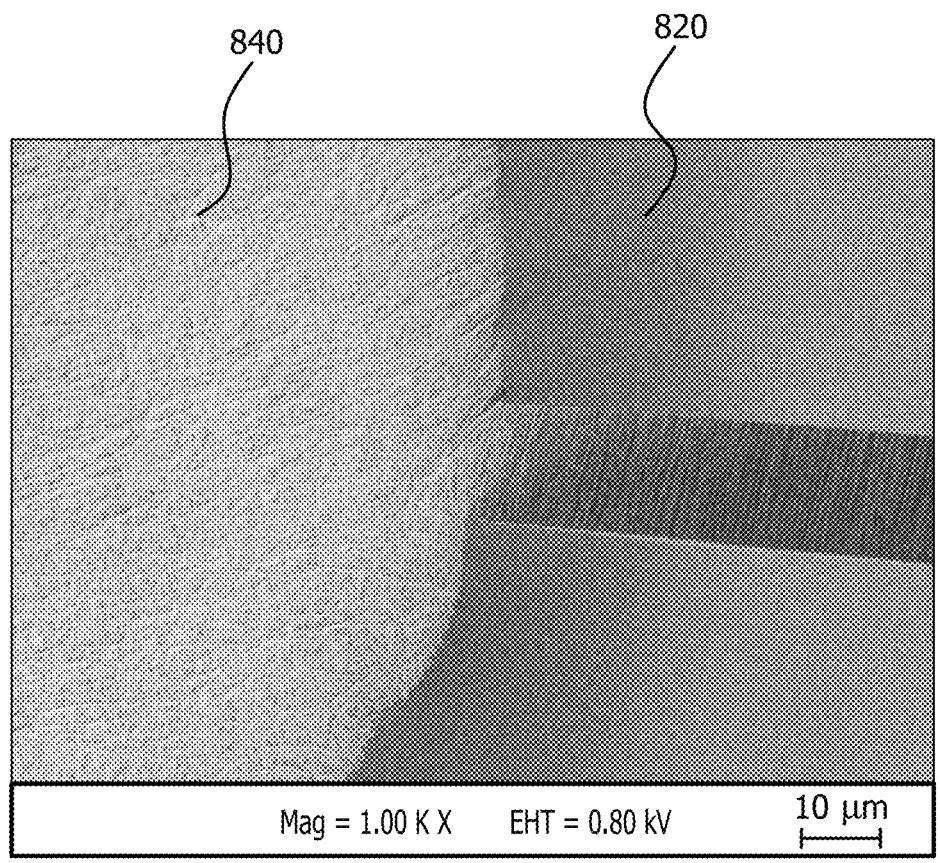
FIG. 8 is an SEM micrograph showing paclitaxel coated from acetonitrile solvent onto a porous substrate comprising ePTFE of a microstructure comprising very highly elongated fibrils.

As seen in FIG. 8, paclitaxel coated from acetonitrile (10 mg/ml) onto ePTFE 840 of a first microstructure comprising very highly elongated fibrils produced a smooth, continuous coating, absent of any high aspect ratio habits. The paclitaxel coating 820 was cracked and separated, orienting and aligning the ePTFE fibrils, indicating the coating had penetrated and embedded into the bulk of the ePTFE substrate. As seen in FIG. 3A, paclitaxel coated from methanol (10 mg/ml) onto ePTFE of a first microstructure comprising very highly elongated fibrils produced a plurality of discrete, individual paclitaxel crystals comprising high aspect ratio habits. The discrete crystals were observed to penetrate and embed into the bulk of the ePTFE substrate, as indicated by elongated ePTFE nodes interconnected among the discrete crystals. The discrete crystals were observed to project from the ePTFE substrate at a projection angle of about 20° to about 90° relative to the substrate. FIG. 3B is a higher magnification of FIG. 3A, showing the elongated ePTFE nodes interconnected among the discrete crystals, and showing the discrete crystals projecting from the ePTFE substrate at a projection angle of about 20° to about 90° relative to the substrate. As seen in FIG. 4, paclitaxel comprising a urea excipient (1:1 mass ratio) coated from methanol (10 mg/ml paclitaxel) onto ePTFE of a first microstructure comprising very highly elongated fibrils produced a plurality of aggregates of paclitaxel/urea crystals comprising high aspect ratio habits. The aggregates were observed to extend into the ePTFE substrate, as indicated by elongated ePTFE nodes interconnected among the aggregates. The aggregates were observed to orient relative to the ePTFE substrate at a projection angle of about 20° to about 90° with many aggregates also laying parallel to the substrate surface.

Example 7

This example describes the SEM visualization and orientation of drug crystals adhered and oriented onto the substrates of Example 2 as coated according to Example 4.

Figure 9:
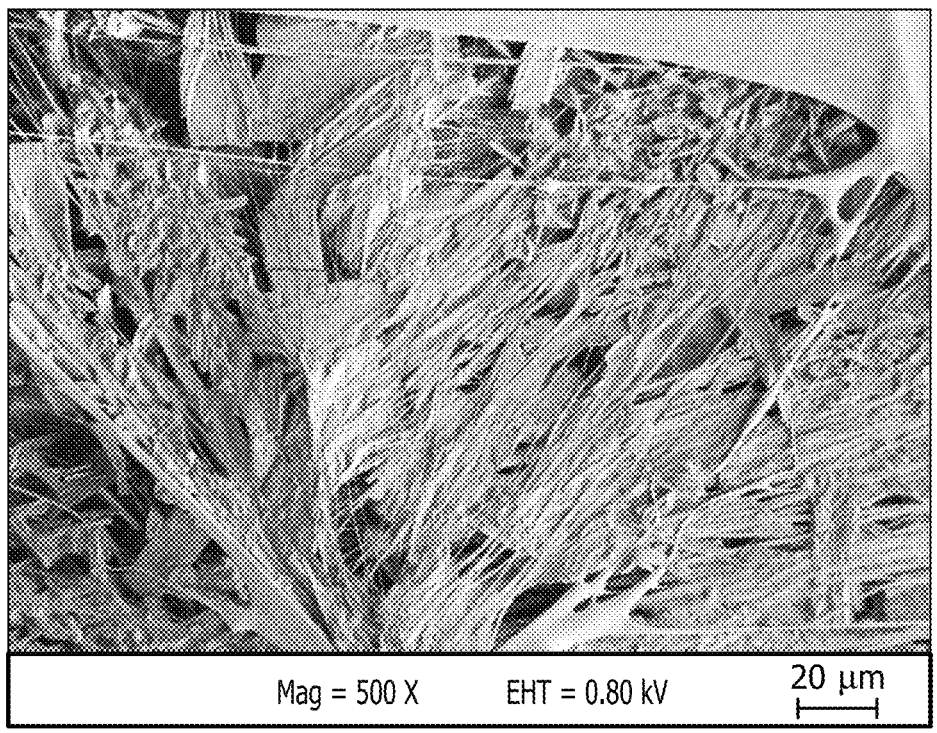
FIG. 9 is an SEM micrograph showing crystalline paclitaxel aggregates comprising a urea excipient coated onto a porous substrate comprising ePTFE of a microstructure comprising very highly elongated nodes interconnected by fibrils.

As seen in FIG. 1, paclitaxel coated from methanol (10 mg/ml) onto ePTFE of a second microstructure comprising very highly elongated nodes interconnected by fibrils produced a plurality of aggregates of paclitaxel crystals comprising high aspect ratio habits. The aggregates were observed to extend into the bulk of the ePTFE substrate, as indicated by elongated ePTFE nodes interconnected throughout the crystal aggregates. The aggregates were observed to orient relative to the ePTFE substrate at a projection angle of about 20° to about 90°. As seen in FIG. 9, paclitaxel comprising urea excipient (1:1 mass ratio) coated from methanol (10 mg/ml paclitaxel) onto ePTFE of a second microstructure comprising very highly elongated nodes interconnected by fibrils produced a plurality of aggregates of paclitaxel/urea crystals comprising multiple habits including high aspect ratio habits, columns, plates, irregular shapes, and the like. The aggregates were observed to extend into the bulk of the ePTFE substrate, as indicated by elongated ePTFE nodes interconnected throughout the crystal aggregates. The aggregates were observed to orient relative to the ePTFE substrate at a projection angle of about 20° to about 90°.

Example 8

This example describes the thermal behavior of high aspect ratio habits of paclitaxel crystals as a function of the substrate.

Representative samples of Examples 5, 6, and 7, were examined under modulated DSC (Model #Q2000, TA Instruments, New Castle, Del.), from −30° to 230° C., using a single heating ramp of 5° C./min, with an oscillation rate of +/−0.5° C. every 40 sec, under nitrogen. Standard T zero pans were used.

Modulated-DSC is capable of discriminating between thermodynamic and kinetic contributions to a crystal's thermal properties during an oscillating heating ramp. The total heat flow is split into reversing (thermodynamic) and non-reversing (kinetic) heat flows. The non-reversing heat flow is those events that do not respond to the oscillating heating ramp, including transitions such as crystal melting, and the like related to crystal purity, recorded as a non-reversing endothermic transition. The reversing heat flow derives from the heat capacity of the sample; phenomena such as crystal polymorph phase de-organization/re-organization, atomic-scale group motion, crystal polymorph phase reorganization, and the like related to crystal perfection, contribute to an excess heat capacity recorded as a reversing exothermic transition. These transitions are reversible events that respond to the oscillating heating ramp.

As seen in FIGS. 6, 1, and 3A, the paclitaxel crystals of each sample have high aspect ratio habits with similar morphologies. Surprisingly, the thermal properties for each were unique and dependent upon the substrate.

For the sample prepared according to Example 5, the DSC thermogram was complex. There were various endothermic events at about 50° C. to about 105° C., indicating loss of water. There was a non-reversing endotherm at about 160° C., followed by a sharp non-reversing exotherm at about 165° C., coincident with reversing excess heat capacity transitions at about 165° C. and at about 170° C. There was a second non-reversing endotherm at about 175° C., again followed by reversing excess heat capacity transitions at about 183° C. and at about 203° C. There was a third non-reversing endotherm at about 207° C.

For the sample prepared according to Example 6, the DSC thermogram was less complex. There was a transition at about 19° C. (ePTFE triclinic-hexagonal transition), followed by various endothermic events at about 50° C. to about 105° C., indicating loss of water. There was a non-reversing endotherm at about 160° C. There was a broad non-reversing exotherm at about 170° C., followed by another non-reversing endotherm at about 215° C.

For the sample prepared according to Example 7, the DSC thermogram was similar to that prepared according to Example 6. For the sample prepared according to Example 7, there was a transition at about 19° C. (ePTFE triclinic-hexagonal transition), followed by various endothermic events at about 50° C. to about 105° C., indicating loss of water. There was a non-reversing endotherm at about 160° C. There was a broad non-reversing exotherm about 175° C., followed by another non-reversing endotherm at about 215° C.

The major thermal events are summarized in Table 1.

TABLE 1

| Temperature (approx ° C.) | Nylon substrate (Example 5) | ePTFE second microstructure (Example 7) | ePTFE first microstructure (Example 6) |
| --- | --- | --- | --- |
| 19 | — | ePTFE transition | ePTFE transition |
| 50-105 | Loss of water (dihydrate) | Loss of water (dihydrate) | Loss of water (dihydrate) |
| 160 | non-reversing endotherm | non-reversing endotherm | non-reversing endotherm |
| 165 | non-reversing exotherm w/ reversing excess heat capacity | — | — |
| 170 | reversing excess heat capacity | non-reversing exotherm | — |
| 175 | non-reversing endotherm | — | non-reversing exotherm |
| 183 | reversing excess heat capacity | — | — |
| 203 | reversing excess heat capacity | — | — |
| 207 | non-reversing endotherm | — | — |
| 215 | — | non-reversing endotherm | non-reversing endotherm |

As can be seen in Table 1, the DSC thermograms are distinct, even though the high aspect ratio habits are similar in appearance. Comparing to nylon, the paclitaxel crystals on both ePTFE microstructures displayed shifts to higher temperatures in their non-reversing endotherms with an absence of reversing excess heat capacity, suggesting that these crystals were more pure and more perfect, even though they share a similar high aspect ratio habit. Furthermore, the high aspect ratio habits of paclitaxel crystals prepared according to Example 6 showed the highest non-reversing exotherm transition, suggesting the discrete, individual crystals, compared to aggregates of crystals, are most perfect.

Without wishing to be bound by any particular theory, the inventors believe the unique microstructure of porous, ePTFE substrates combined with the appropriate solvent and processing conditions, act as a template for the crystallization of drug preferentially as high aspect ratio habits that extend into the porous ePTFE at a projection angle of about 20° to about 90°. The inventors believe ePTFE's high surface area, high vapor transmission rate, and relatively high thermal conductivity, provide means for drug solvation and mass transport, and means for a steep thermal gradient, necessary for the growth of high aspect ratio habit crystals that are fully or partially embedded at a projection angle of about 20° C. to about 90°.

This Example suggests that the substrate surprisingly and unexpectedly affects embedding of the high aspect ratio drug crystals in the bulk of the substrate, the orientation of crystals relative to the substrate, and the purity and perfection of the crystal structure.

Example 9

This Example describes the SEM visualization and orientation of drug crystals embedded and oriented onto the substrates of Examples 1 and 2, as coated according to Example 4 after sterilization.

Figure 22:
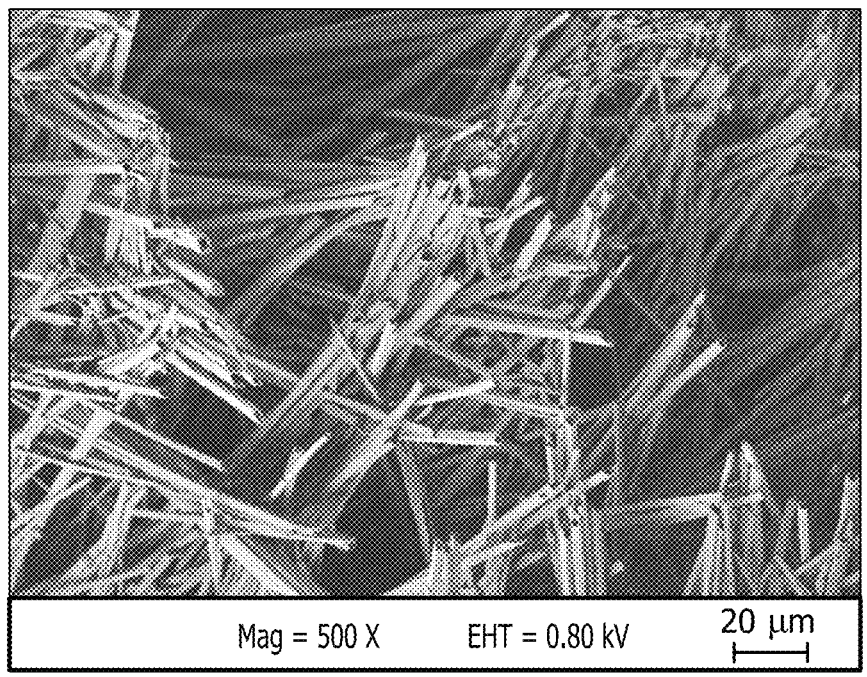
FIG. 22 is a SEM micrograph showing discrete hollow acicular paclitaxel crystals coated from methanol onto a porous substrate comprising ePTFE of a microstructure comprising very highly elongated fibrils, after ethylene oxide sterilization.
Figure 23:
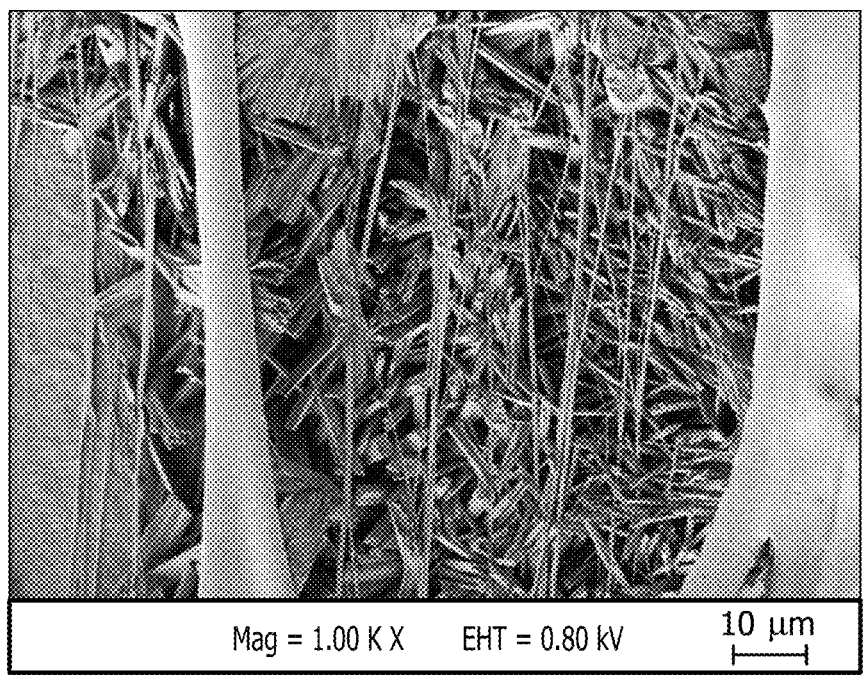
FIG. 23 is a SEM micrograph showing discrete hollow acicular paclitaxel crystals coated onto a porous substrate comprising ePTFE of a microstructure comprising very highly elongated fibrils, after ethylene oxide sterilization.

Representative samples of Examples 6 and 7 were exposed to ethylene oxide sterilization, under conditions of conditioning for about 24 hr, an EtO gas dwell time of about 22 hr, a set point temperature of 64° C., and an aeration time of about 12 hrs. The samples were then visualized with SEM. The acicular habits of the paclitaxel crystals, their geometry, their penetration into the ePTFE microporous substrate, and their angles of projection, were unaffected by the ethylene oxide sterilization. For example, FIG. 22 is an SEM micrograph of the coated substrate as seen in FIG. 3A after ethylene oxide sterilization. For another example, FIG. 23 is a SEM micrograph of the coated substrate as seen in FIG. 1 after ethylene oxide sterilization.

Example 10

This example describes the ex vivo transfer of drug crystals from an ePTFE substrate to a vascular tissue.

Substrates of ePTFE of Examples 1 and 2 were coated with paclitaxel (10 mg/ml) or paclitaxel/urea (1:1 mass ratio; 10 mg/ml paclitaxel) according to Example 4. The substrates were examined under SEM to confirm the presence of high aspect paclitaxel crystal habits embedded and oriented in the ePTFE microstructure.

A freshly harvested carotid artery from >2 yr old swine (Animal Technologies Inc., Tyler Tex.) was slit axially using a scalpel blade, cut lengthwise into portions, everted, and the portions adhered to a glass microscope slide using cyanoacrylate adhesive (Loctite), luminal aspect up. Tissue portions were kept wet using phosphate-buffered saline until use.

The glass microscope slide containing the artery portion was gently placed, tissue side down, upon the coated ePTFE substrate, to expose the endothelial layer to the paclitaxel crystals. The endothelial layer was compressed at about 5.4 atm against the coated ePTFE substrate for 60 sec. The glass microscope slide containing the artery portion was then examined under SEM.

FIG. 10 is a representative SEM micrograph of the artery portion after exposure for 60 sec at 5.4 atm to a coated ePTFE substrate. The "cobblestone" morphology of the endothelial layer is visible to the left. The endothelial layer to the right is extensively covered with engaged and embedded paclitaxel crystals, indicating transfer from the ePTFE substrate to the vascular tissue. The high aspect ratio of the crystals is intact, indicating mechanical stability and mechanical strength of the crystals during the 60 sec compression at 5.4 atm. All examined ePTFE substrates of Example 1 and Example 2, coated with paclitaxel or paclitaxel/urea according to Example 4, showed similar results.

Example 11

This Example describes the general procedure for the preparation of drug crystals adhered or otherwise embedded onto a substrate using vapor annealing.

The substrates on glass slides of Example 4 were inserted into a 50 ml polypropylene centrifuge tube (VWR). 100 µl of solvent (methanol ACS grade, ethanol 200 proof absolute grade, acetonitrile ACS grade, or deionized water) was carefully pipetted into the tube's conical base, ensuring no contact with the glass slide, the tube tightly capped, and the tube laid on its side such the substrate faced up. The evaporating solvent saturated the tube's interior atmosphere with solvent vapor. Samples were maintained in this condition for 48 hrs at about 20° C. at an ambient atmospheric pressure of about 773 mm Hg.

Example 12

This example describes the SEM visualization and orientation of drug crystals adhered to and oriented onto the substrates of Example 1 as coated according to Example 11.

FIGS. 11A to 11D are the SEM micrographs of paclitaxel coated from methanol (30 mg/ml) onto ePTFE of a first microstructure comprising very highly elongated fibrils.

FIG. 11A is paclitaxel coated onto ePTFE without a vapor annealing step, and produced a plurality of aggregates of paclitaxel crystals comprising hollow acicular habits. The crystals and aggregates were observed to penetrate into the ePTFE substrate, as indicated by elongated ePTFE nodes interconnected among the crystal aggregates. The aggregates were observed to be projecting from the ePTFE substrate at a projection angle of about 20° to about 90°.

Figure 11B:
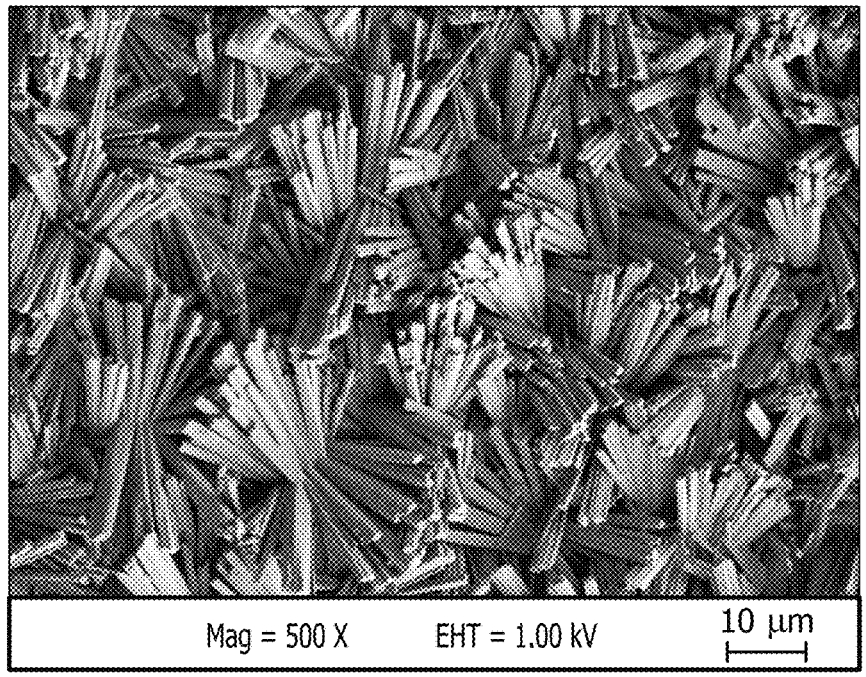

FIG. 11B is paclitaxel coated onto ePTFE with an acetonitrile vapor annealing step, and produced a plurality of aggregates of paclitaxel crystals comprising acicular habits. It is unclear if these habits are hollow with sealed ends or if the hollow habit was transformed into a solid habit. The crystals and aggregates were observed to penetrate into the ePTFE substrate, as indicated by elongated ePTFE nodes interconnected among the crystal aggregates. The aggregates were observed to orient relative to the ePTFE substrate at a projection angle of about 20° to about 90°.

Figure 11C:
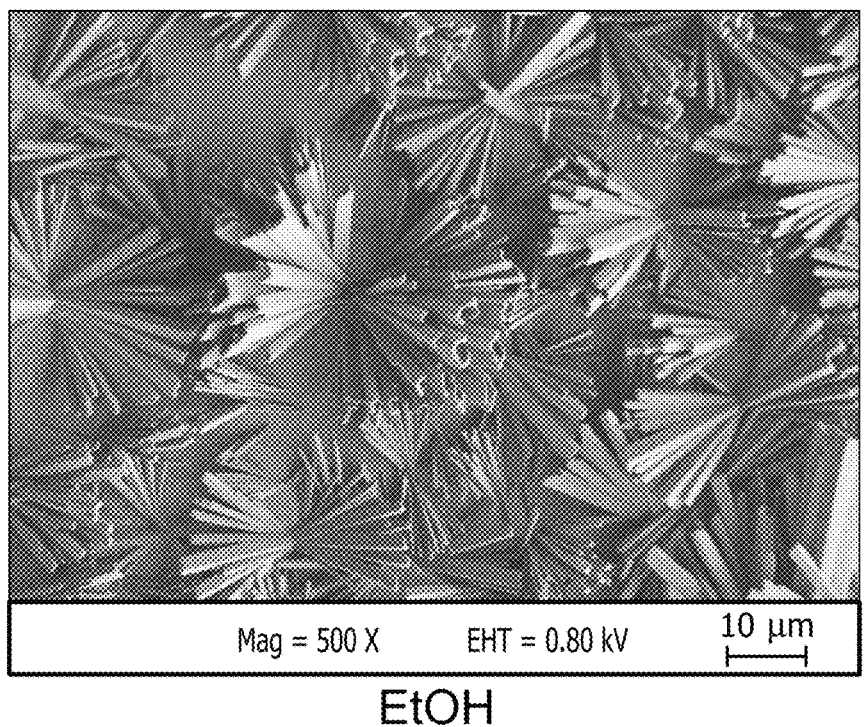

FIG. 11C is paclitaxel coated onto ePTFE with an ethanol vapor annealing step, and produced a plurality of aggregates of paclitaxel crystals comprising hollow acicular habits. The crystals and aggregates were observed to penetrate into the ePTFE substrate, as indicated by elongated ePTFE nodes interconnected among the crystal aggregates. The aggregates were observed to orient relative to the ePTFE substrate at a projection angle of about 20° to about 90°.

Figure 11D:
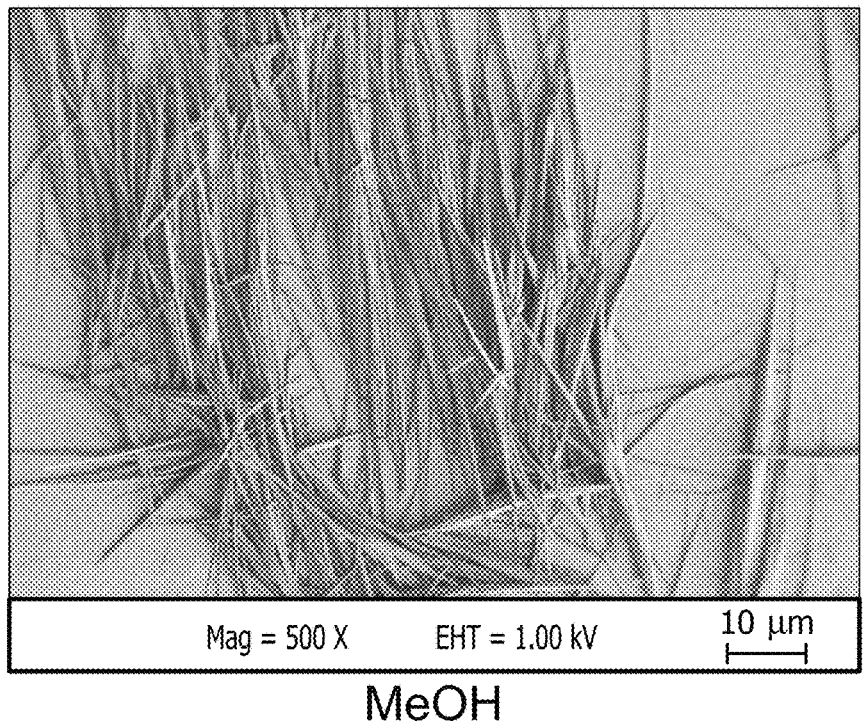

FIG. 11D is paclitaxel coated onto ePTFE with a methanol vapor annealing step, and produced a plurality of discrete paclitaxel crystals comprising acicular habits. The crystals were observed to penetrate and embed into the bulk of the ePTFE substrate, as indicated by elongated ePTFE nodes interconnected among the crystals. The crystals were observed to orient relative to the ePTFE substrate at a projection angle of about 20° to about 90°, with many crystals also laying parallel to the substrate surface.

FIGS. 12A to 12D are the SEM micrographs of paclitaxel coated from acetone (30 mg/ml) onto ePTFE of a first microstructure comprising very highly elongated fibrils.

Figure 12A:
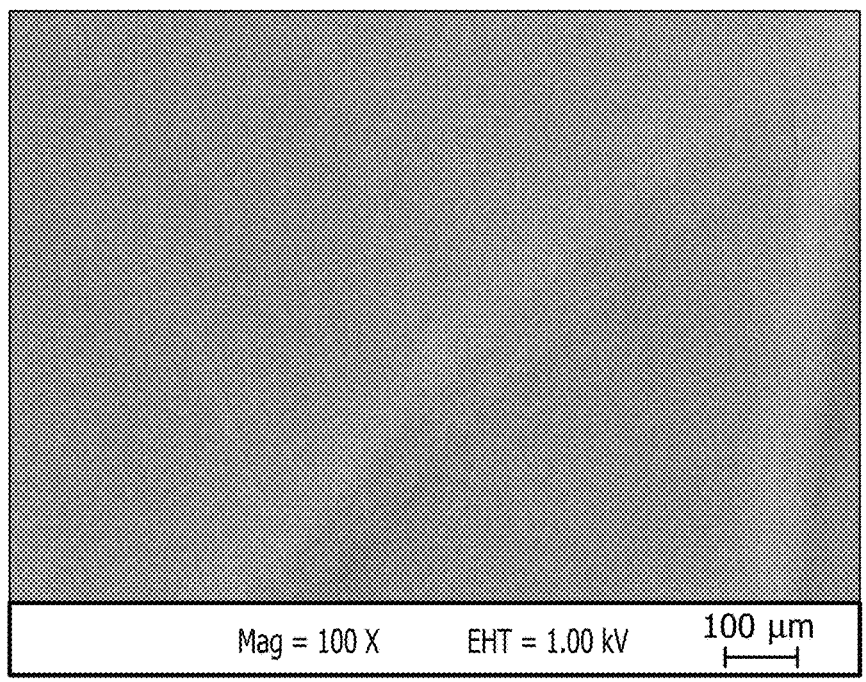
FIGS. 12A to 12D are SEM micrographs showing paclitaxel crystals of various habits coated from acetone solvent and various vapor annealing, onto a porous substrate comprising ePTFE of a microstructure comprising very highly elongated fibrils.

FIG. 12A is paclitaxel coated onto ePTFE without a vapor annealing step, and produced a smooth, continuous coating, absent of any high aspect ratio habits.

Figure 12B:
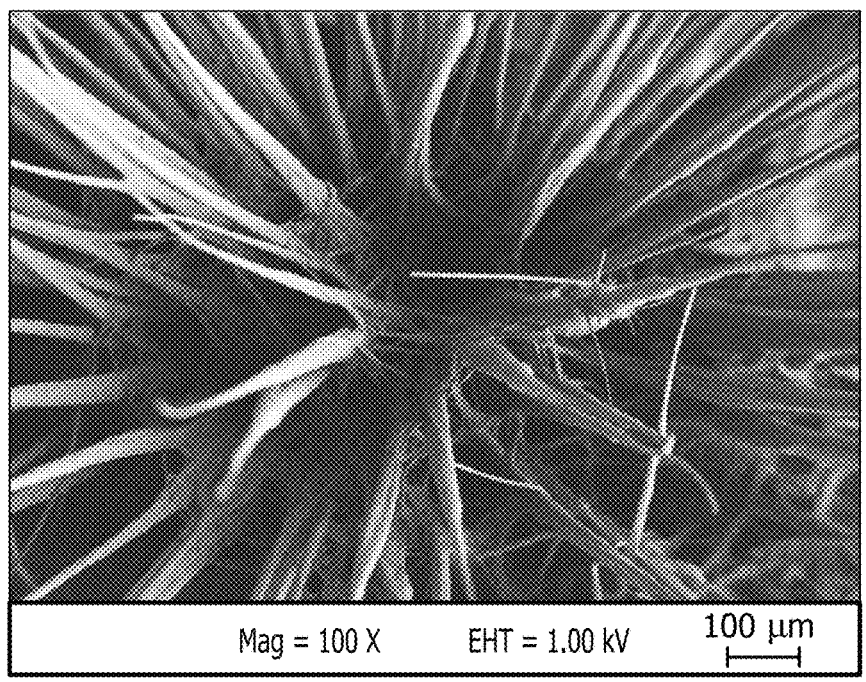

FIG. 12B is paclitaxel coated onto ePTFE with an acetonitrile vapor annealing step, and produced a plurality of aggregates of paclitaxel crystals comprising thin, irregular acicular habits. The crystals and aggregates were observed to penetrate into the bulk of the ePTFE substrate, as indicated by elongated ePTFE nodes interconnected throughout the crystal aggregates. The aggregates were observed to orient relative to the ePTFE substrate at a projection angle of about 20° to about 90°.

Figure 12C:
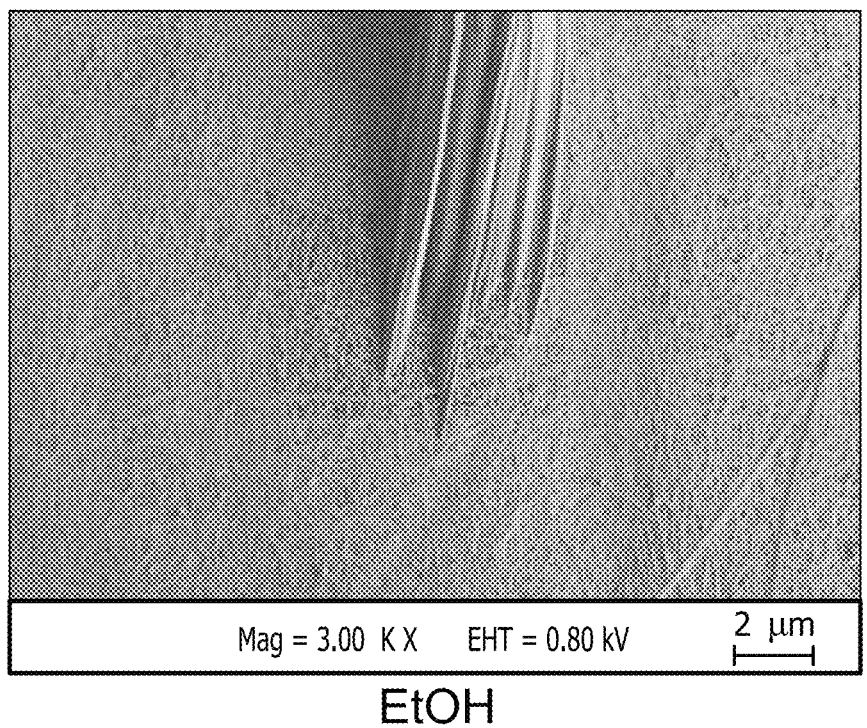

FIG. 12C is paclitaxel coated onto ePTFE with an ethanol vapor annealing step, and produced a plurality of aggregates of paclitaxel crystals comprising acicular habits. The crystals and aggregates were observed to penetrate into the bulk of the ePTFE substrate, as indicated by elongated ePTFE nodes interconnected throughout the crystal aggregates. The aggregates were observed to orient relative to the ePTFE substrate at a projection angle of about 20° to about 90°.

Figure 12D:
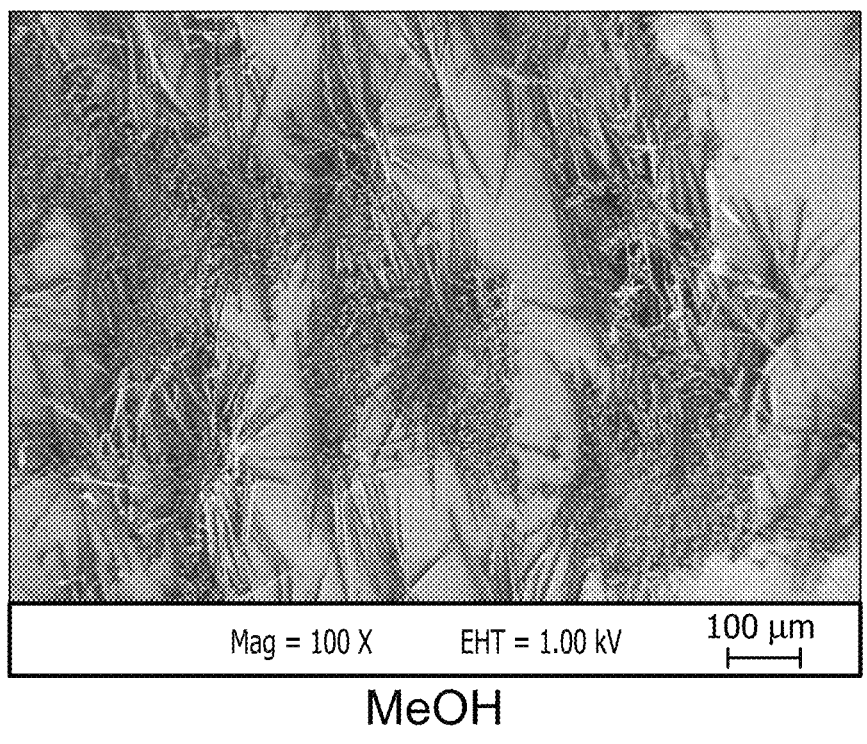

FIG. 12D is paclitaxel coated onto ePTFE with a methanol vapor annealing step, and produced a plurality of discrete paclitaxel crystals comprising acicular habits. The crystals were observed to penetrate into the bulk of the ePTFE substrate, as indicated by elongated ePTFE nodes interconnected throughout the crystals. The crystals were observed to orient relative to the ePTFE substrate at a projection angle of about 20° to about 90°.

FIGS. 13A to 13D are the SEM micrographs of paclitaxel coated from methanol (30 mg/ml) comprising urea (8:1 mass ratio paclitaxel:urea) onto ePTFE of a first microstructure comprising very highly elongated fibrils.

Figure 13A:
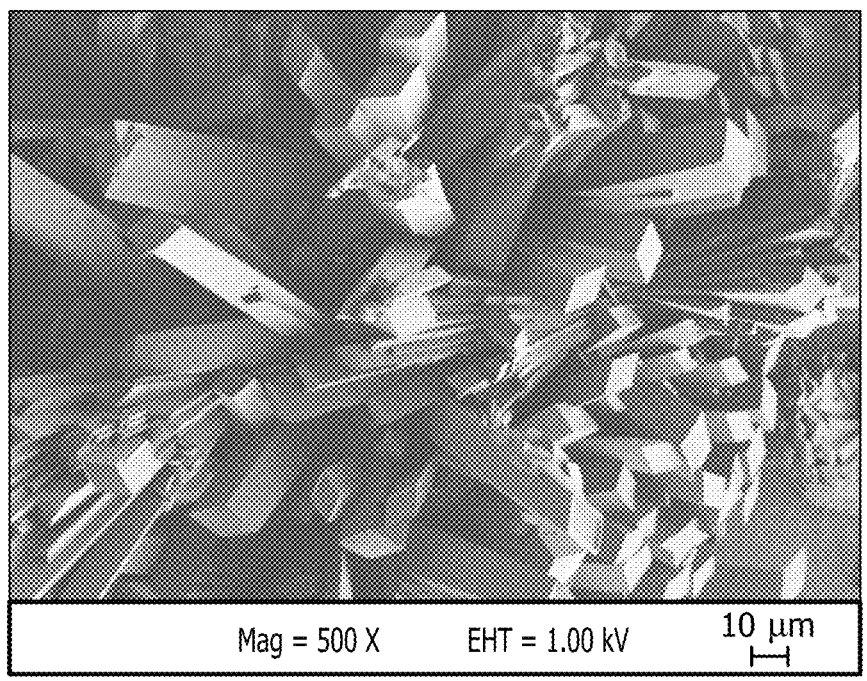
FIGS. 13A to 13D are SEM micrographs showing paclitaxel crystals of various habits comprising a urea excipient coated from methanol solvent and various vapor annealing, onto a porous substrate comprising ePTFE of a microstructure comprising very highly elongated fibrils.

FIG. 13A is paclitaxel coated onto ePTFE without a vapor annealing step, and produced a plurality of aggregates of paclitaxel crystals comprising acicular habits. The crystals and aggregates were observed to penetrate into the bulk of the ePTFE substrate, as indicated by elongated ePTFE nodes interconnected throughout the crystal aggregates. The aggregates were observed to orient relative to the ePTFE substrate at a projection angle of about 20° to about 90°.

Figure 13B:
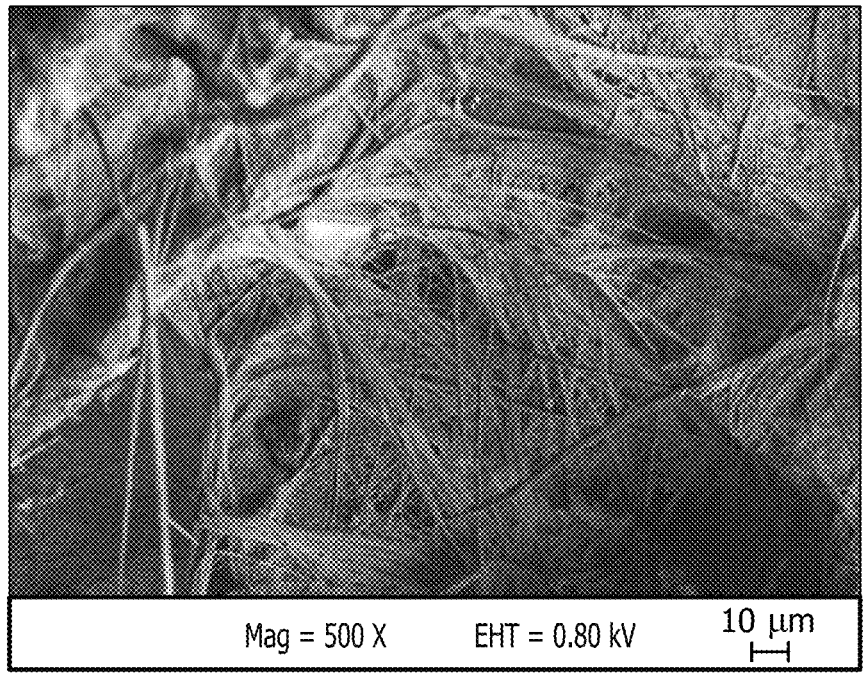

FIG. 13B is paclitaxel coated onto ePTFE with an acetonitrile vapor annealing step, and produced a plurality of paclitaxel crystals comprising elongated, irregular acicular habits in a dense mat. The crystals were observed to penetrate into the bulk of the ePTFE substrate, as indicated by elongated ePTFE nodes interconnected throughout the crystals. The crystals were observed to orient relative to the ePTFE substrate at a projection angle of about 20° to about 90°, with many crystals also laying parallel to the substrate surface.

Figure 13C:
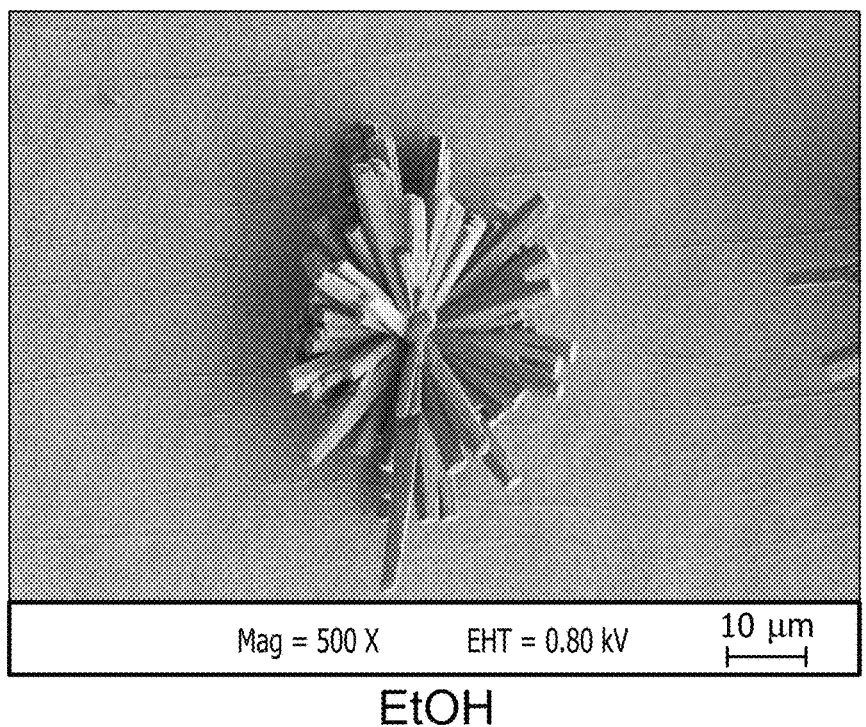

FIG. 13C is paclitaxel coated onto ePTFE with an ethanol vapor annealing step, and produced a plurality of aggregates of paclitaxel crystals comprising acicular habits. The crystals and aggregates were observed to penetrate into the bulk of the ePTFE substrate, as indicated by elongated ePTFE nodes interconnected throughout the crystal aggregates. The aggregates were observed to orient relative to the ePTFE substrate at a projection angle of about 20° to about 90°.

Figure 13D:
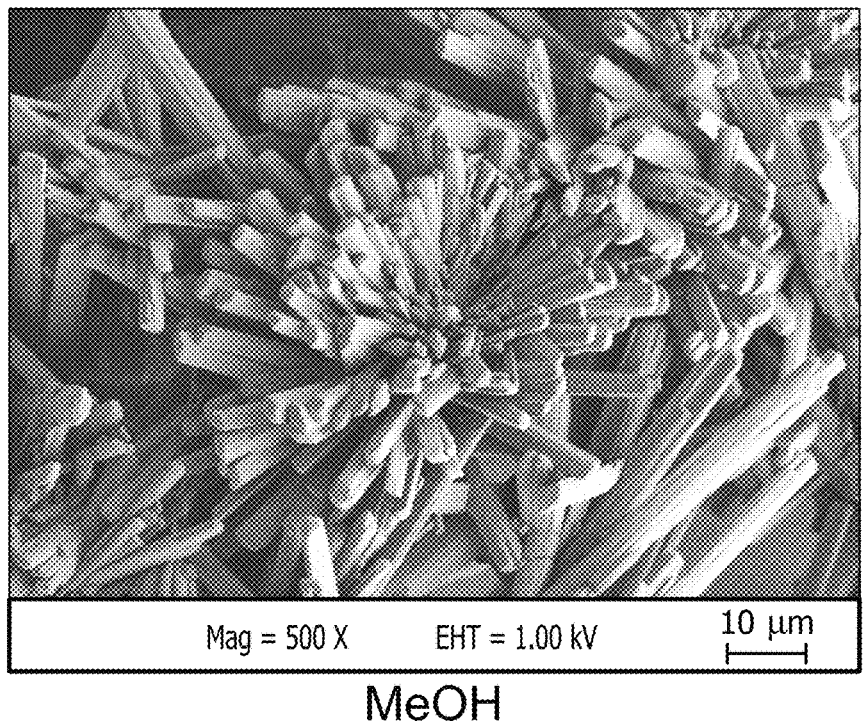

FIG. 13D is paclitaxel coated onto ePTFE with a methanol vapor annealing step, and produced a plurality of discrete paclitaxel crystals comprising acicular habits. The crystals were observed to penetrate into the bulk of the ePTFE substrate, as indicated by elongated ePTFE nodes interconnected throughout the crystals. The crystals were observed to orient relative to the ePTFE substrate at a projection angle of about 20° to about 90°, with many crystals also laying parallel to the substrate surface.

In this Example, a smooth glassy coating was transformed using vapor annealing into crystals that project from the porous substrate at a projection angle of about 20° to about 90°.

Example 13

This example describes the SEM visualization and orientation of drug crystals embedded and oriented onto the substrates of Example 2 as coated according to Example 11.

FIG. 14 is the SEM micrographs of paclitaxel coated from methanol (30 mg/ml) onto ePTFE of a second microstructure comprising very highly elongated nodes interconnected by fibrils.

Figure 14A:
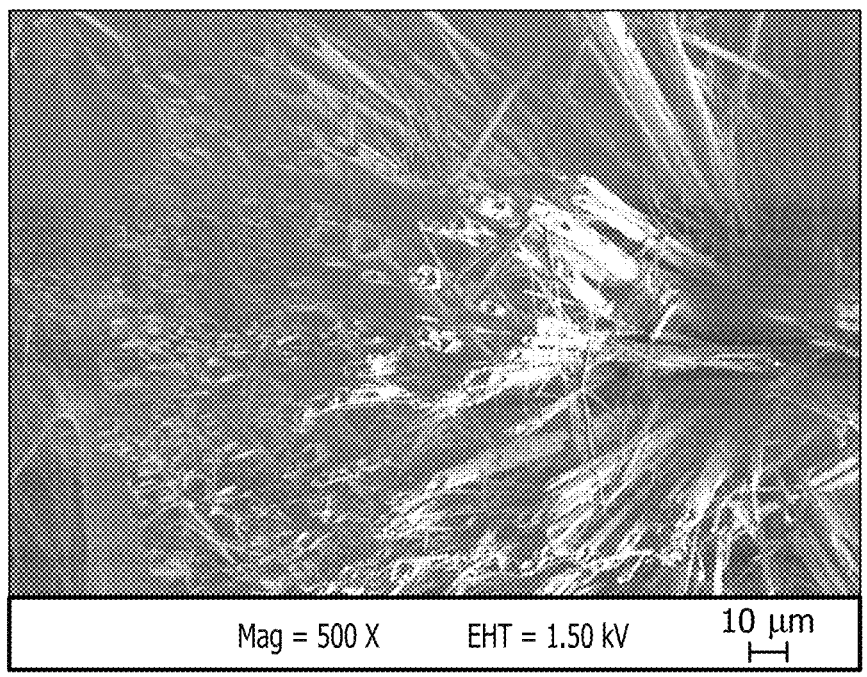
FIGS. 14A to 14D are SEM micrographs showing paclitaxel crystals of various habits coated from methanol solvent and various vapor annealing, onto a porous substrate comprising ePTFE of microstructure comprising very highly elongated nodes interconnected by fibrils.

FIG. 14A is paclitaxel coated onto ePTFE without a vapor annealing step, and produced a plurality of aggregates of paclitaxel crystals comprising hollow acicular habits. The crystals and aggregates were observed to penetrate and embed into the bulk of the ePTFE substrate, as indicated by elongated ePTFE nodes interconnected throughout the crystal aggregates. The aggregates were observed to orient relative to the ePTFE substrate at a projection angle of about 20° to about 90°.

Figure 14B:
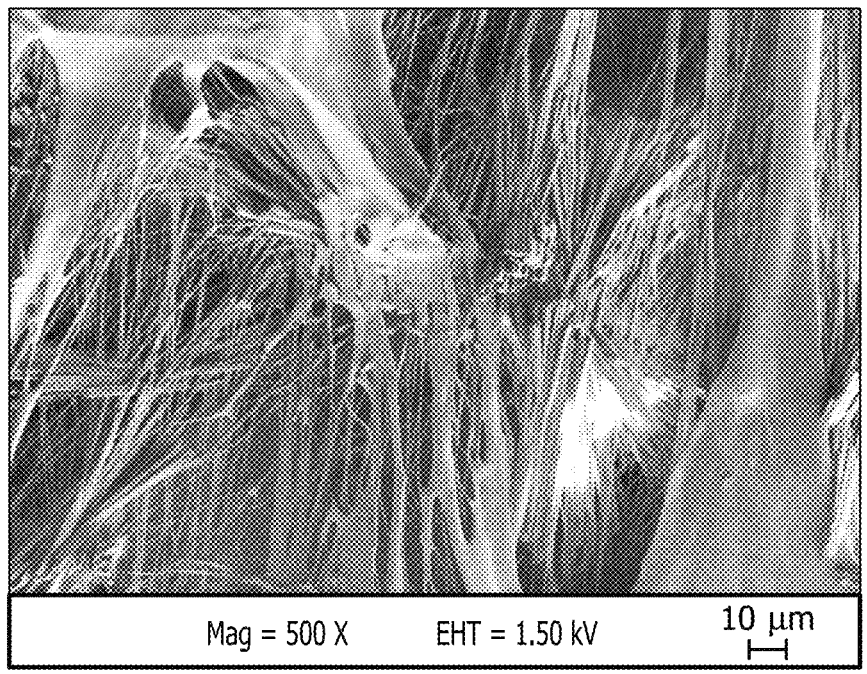

FIG. 14B is paclitaxel coated onto ePTFE with an acetonitrile vapor annealing step, and produced a plurality of paclitaxel crystals comprising acicular habits. It is unclear if these habits are hollow with sealed ends or if the hollow habit was transformed into a solid habit. The crystals and aggregates were observed to penetrate and embed into the bulk of the ePTFE substrate, as indicated by elongated ePTFE nodes interconnected throughout the crystal aggregates. The aggregates were observed to orient relative to the ePTFE substrate at a projection angle of about 20° to about 90°.

Figure 14C:
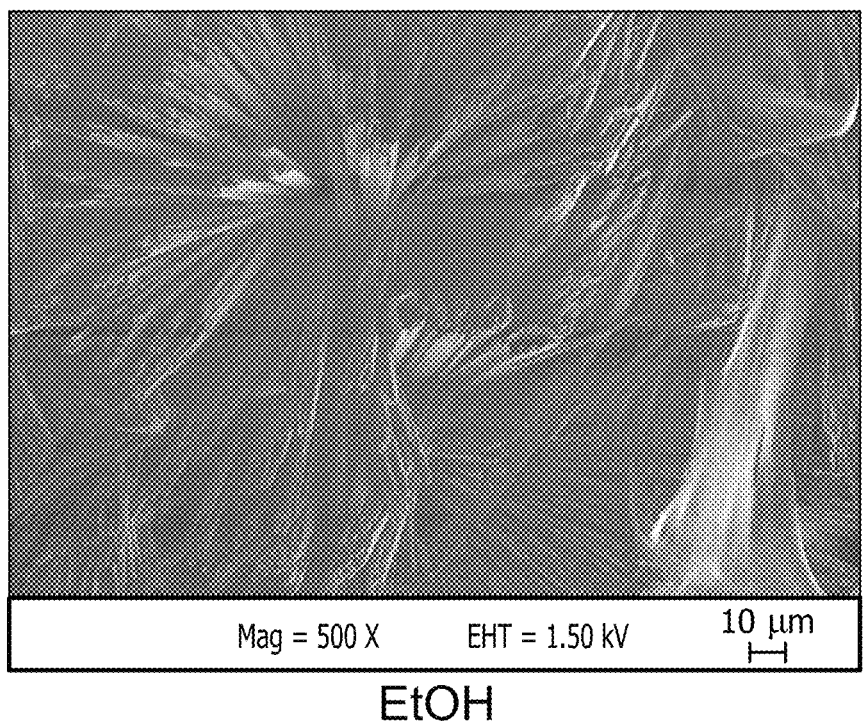

FIG. 14C is paclitaxel coated onto ePTFE with an ethanol vapor annealing step, and produced a plurality of aggregates of paclitaxel crystals comprising acicular hollow habits. The tips of the crystals appeared irregular. The crystals and aggregates were observed to penetrate into the ePTFE substrate, as indicated by elongated ePTFE nodes interconnected among the crystal aggregates. The aggregates were observed to orient relative to the ePTFE substrate at a projection angle of about 20° to about 90°.

Figure 14D:
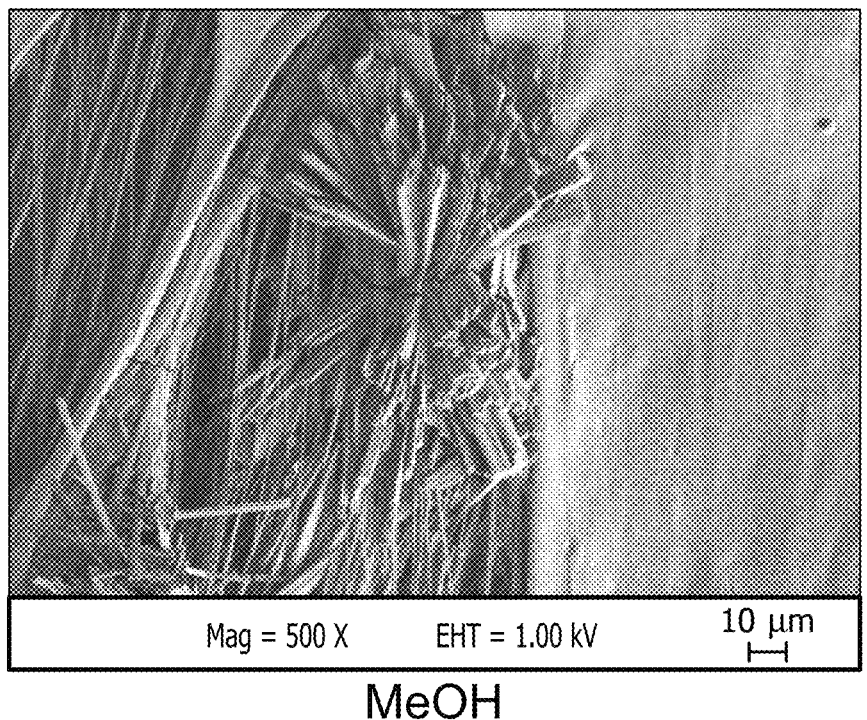

FIG. 14D is paclitaxel coated onto ePTFE with a methanol vapor annealing step, and produced a plurality of paclitaxel crystals comprising acicular habits. It is unclear if these habits are hollow with sealed ends or if the hollow habit was transformed into a solid habit. The crystals and aggregates were observed to penetrate into the ePTFE substrate, as indicated by elongated ePTFE nodes interconnected among the crystal aggregates. The aggregates were observed to orient relative to the ePTFE substrate at a projection angle of about 20° to about 90°.

FIGS. 15A to 15D are the SEM micrographs of paclitaxel coated from acetone (30 mg/ml) onto ePTFE of a second microstructure comprising very highly elongated nodes interconnected by fibrils.

Figure 15A:
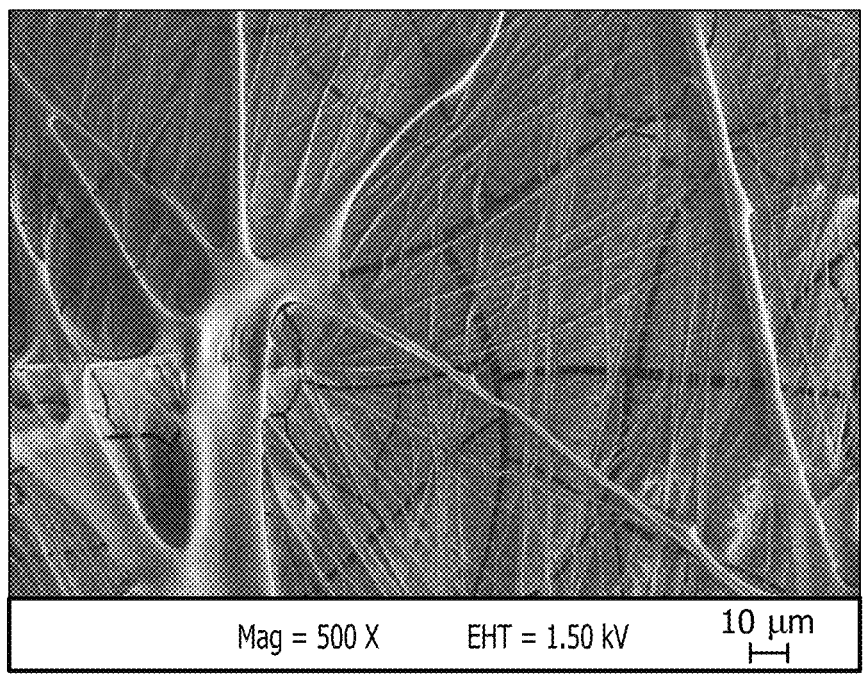
FIGS. 15A to 15D are SEM micrographs showing paclitaxel crystals of various habits coated from acetone solvent and various vapor annealing, onto a porous substrate comprising ePTFE of microstructure comprising very highly elongated nodes interconnected by fibrils.

FIG. 15A is paclitaxel coated onto ePTFE without a vapor annealing step, and produced a smooth, continuous coating with numerous cracks, embedded into the bulk of the ePTFE, and absent of any high aspect ratio habits.

Figure 15B:
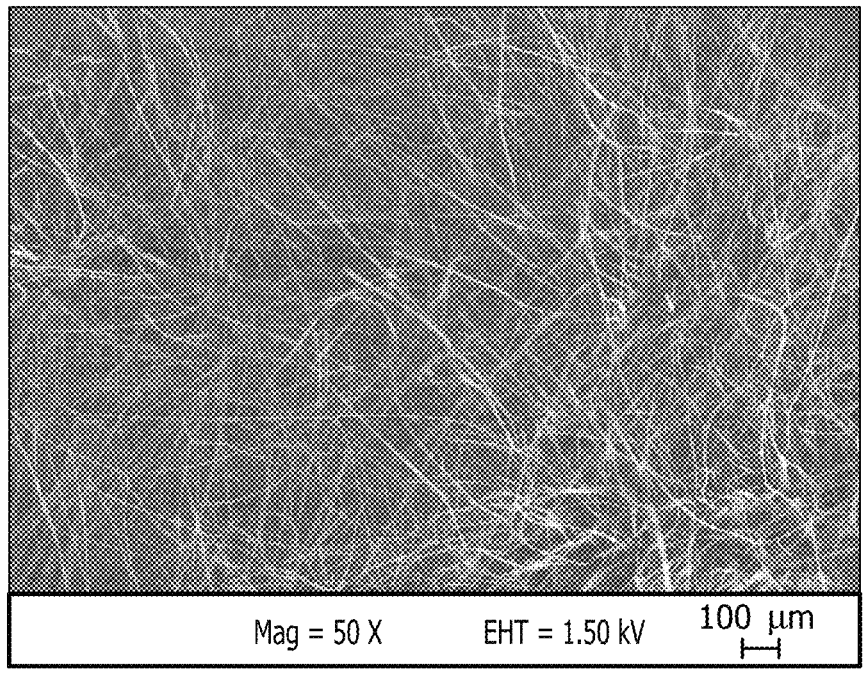

FIG. 15B is paclitaxel coated onto ePTFE with an acetonitrile vapor annealing step, and produced a plurality of aggregates of paclitaxel crystals comprising thin, elongated, irregular acicular habits. The crystals and aggregates were observed to penetrate into the ePTFE substrate, as indicated by elongated ePTFE nodes interconnected among the crystal aggregates. The aggregates were observed to orient relative to the ePTFE substrate at a projection angle of about 20° to about 90°.

Figure 15C:
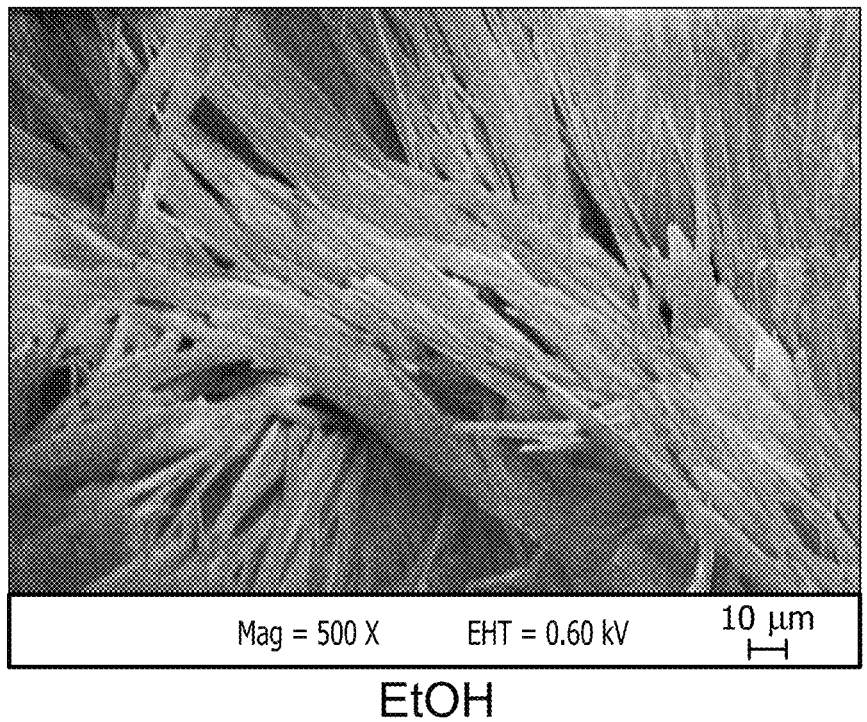

FIG. 15C is paclitaxel coated onto ePTFE with an ethanol vapor annealing step, and produced a plurality of aggregates of paclitaxel crystals comprising acicular habits. The crystals and aggregates were observed to penetrate into the ePTFE substrate, as indicated by elongated ePTFE nodes interconnected among the crystal aggregates. The aggregates were observed to orient relative to the ePTFE substrate at a projection angle of about 20° to about 90°.

Figure 15D:
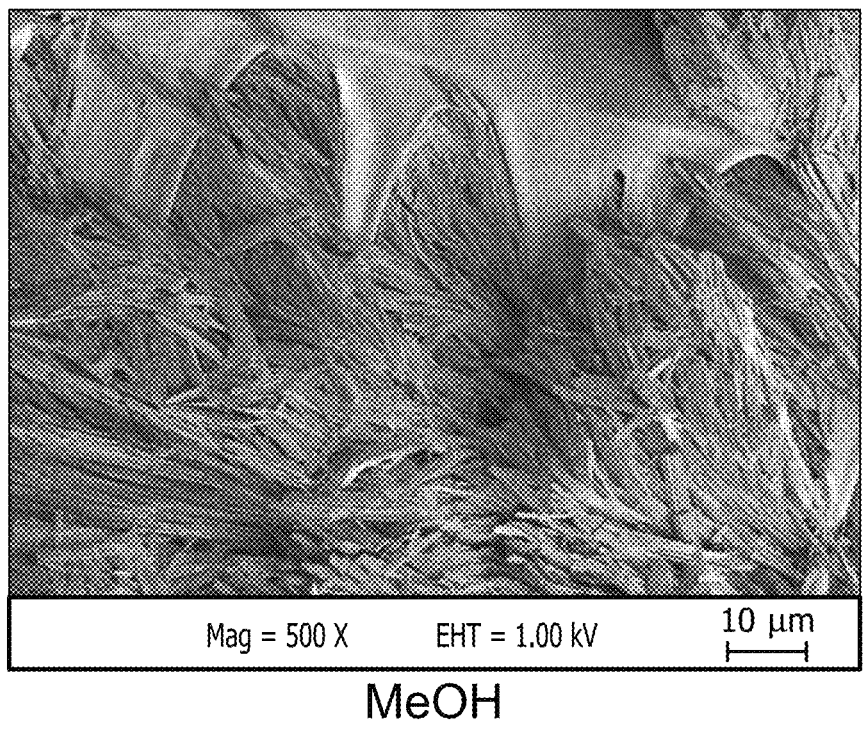

FIG. 15D is paclitaxel coated onto ePTFE with a methanol vapor annealing step, and produced a plurality of discrete paclitaxel crystals comprising acicular habits in a dense mat. The crystals were observed to penetrate into the ePTFE substrate, as indicated by elongated ePTFE nodes interconnected among the crystals. The crystals were observed to orient relative to the ePTFE substrate at a projection angle of about 20° to about 90°, with many crystals also laying parallel to the substrate surface.

FIGS. 16A to 16D is the SEM micrographs of paclitaxel coated from methanol (30 mg/ml) comprising urea (8:1 mass ratio paclitaxel:urea) onto ePTFE of a second microstructure comprising very highly elongated nodes interconnected by fibrils.

Figure 16A:
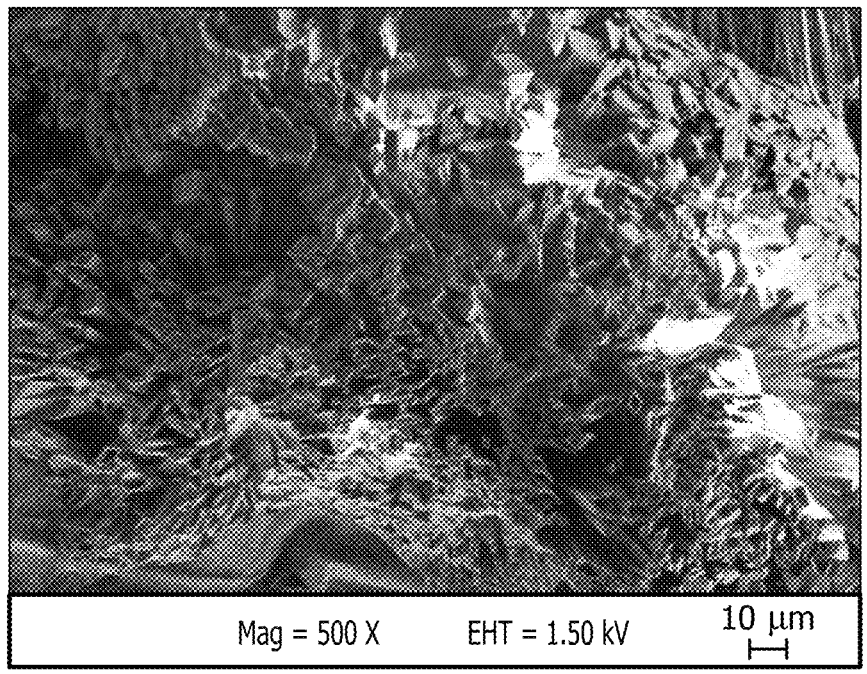
FIGS. 16A to 16D are SEM micrographs showing paclitaxel crystals of various habits comprising a urea excipient coated from methanol solvent and various vapor annealing, onto a porous substrate comprising ePTFE of microstructure comprising very highly elongated nodes interconnected by fibrils.

FIG. 16A is paclitaxel coated onto ePTFE without a vapor annealing step, and produced a plurality of paclitaxel crystals comprising acicular habits fused into aggregates. The crystals and aggregates were observed to penetrate into the ePTFE substrate, as indicated by elongated ePTFE nodes interconnected among the crystal aggregates. The aggregates were observed to orient relative to the ePTFE substrate at a projection angle of about 20° to about 90°.

Figure 16B:
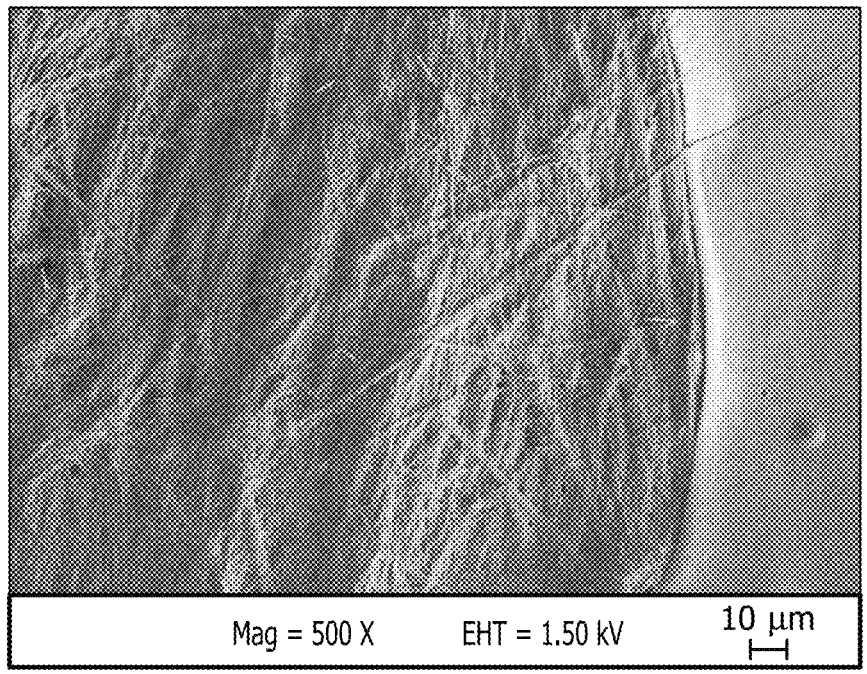

FIG. 16B is paclitaxel coated onto ePTFE with an acetonitrile vapor annealing step, and produced a plurality of paclitaxel crystals comprising elongated, irregular acicular habits in a dense mat. The crystals were observed to penetrate into the ePTFE substrate, as indicated by elongated ePTFE nodes interconnected among the crystals. The crystals were observed to orient relative to the ePTFE substrate at a projection angle of about 20° to about 90°, with many crystals also laying parallel to the substrate surface.

Figure 16C:
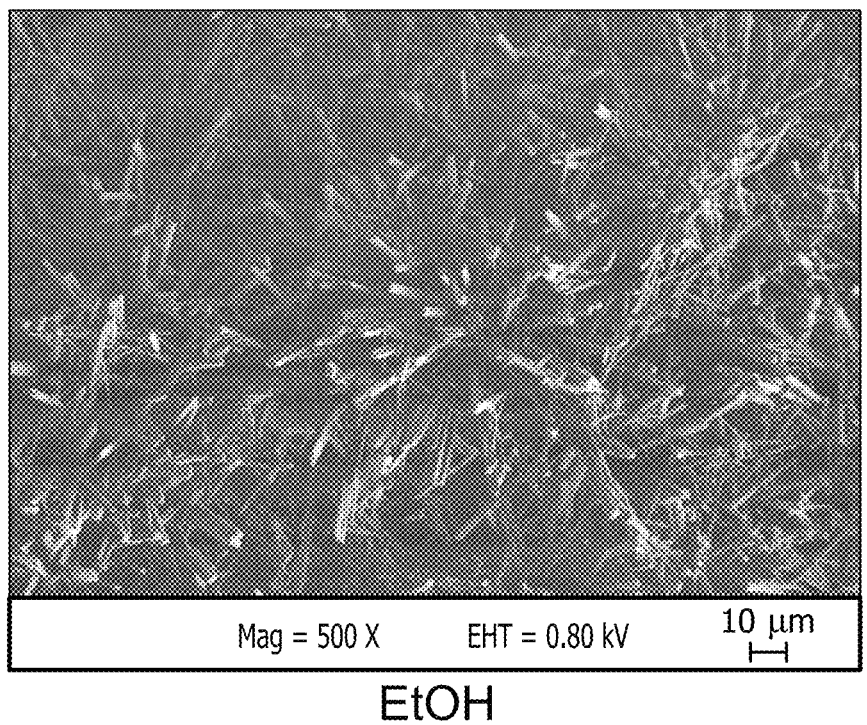

FIG. 16C is paclitaxel coated onto ePTFE with an ethanol vapor annealing step, and produced a plurality of discrete paclitaxel crystals comprising acicular habits. The crystals were observed to penetrate into the ePTFE substrate, as indicated by elongated ePTFE nodes interconnected among the crystal aggregates. The crystals were observed to orient relative to the ePTFE substrate at a projection angle of about 20° to about 90°.

Figure 16D:
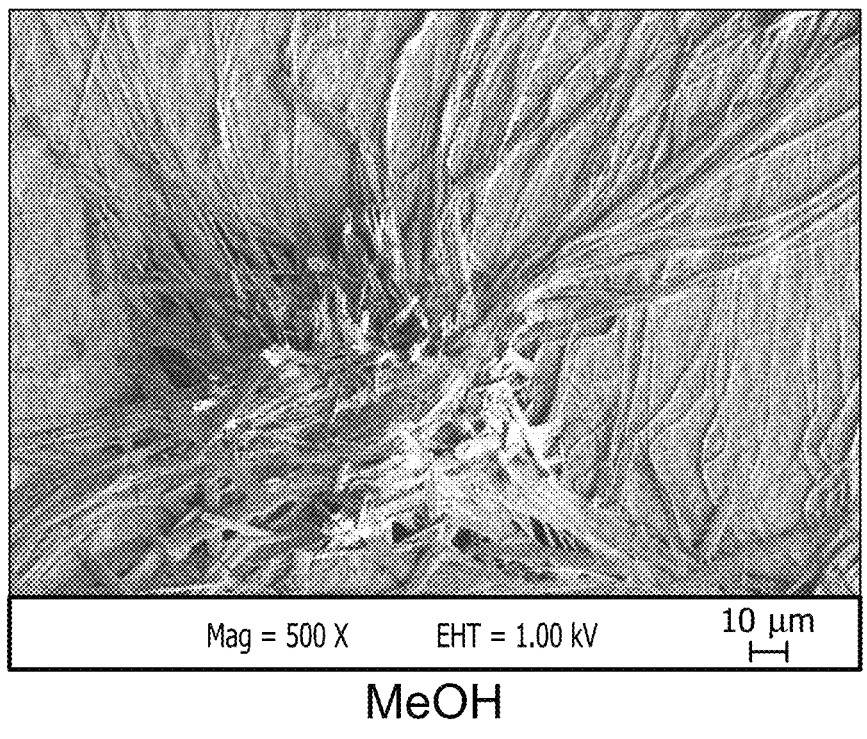

FIG. 16D is paclitaxel coated onto ePTFE with a methanol vapor annealing step, and produced a plurality of paclitaxel crystals comprising elongated, irregular acicular habits in a dense mat. The crystals were observed to penetrate into the ePTFE substrate, as indicated by elongated ePTFE nodes interconnected among the crystals. The crystals were observed to orient relative to the ePTFE substrate at a projection angle of about 20° to about 90°, with many crystals also laying parallel to the substrate surface.

Figure 17A:
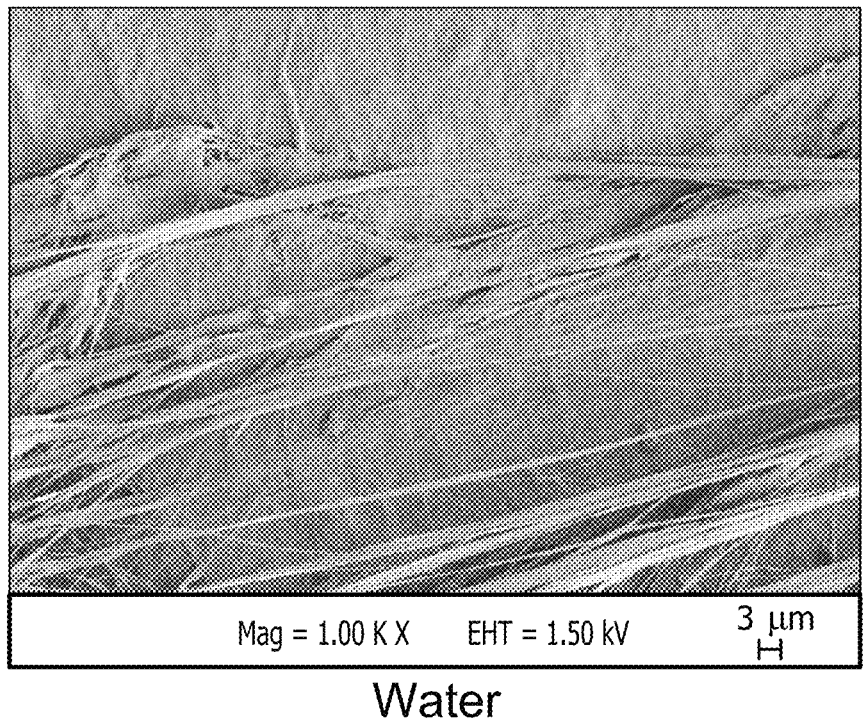
FIGS. 17A to 17B are SEM micrographs showing paclitaxel crystals of various habits coated from acetonitrile solvent and various vapor annealing, onto a porous substrate comprising ePTFE of microstructure comprising very highly elongated nodes interconnected by fibrils.
Figure 17B:
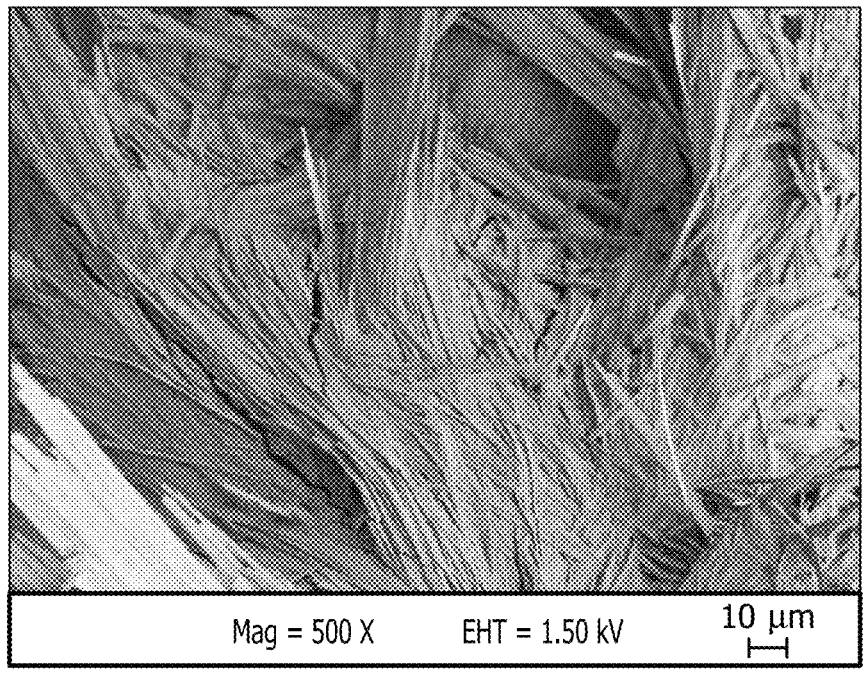

FIGS. 17A to 17B are the SEM micrographs of paclitaxel coated from acetonitrile (30 mg/ml) onto ePTFE of a second microstructure comprising very highly elongated nodes interconnected by fibrils.

FIG. 17A is paclitaxel coated onto ePTFE with a water vapor annealing step, and produced a smooth, continuous coating on the ePTFE, absent of any high aspect ratio habits.

FIG. 17B is paclitaxel coated onto ePTFE with an acetonitrile vapor annealing step, and produced a plurality of paclitaxel crystals comprising elongated, irregular acicular habits in a dense mat. The crystals were observed to penetrate into the ePTFE substrate, as indicated by elongated ePTFE nodes interconnected among the crystals. The crystals were observed to orient relative to the ePTFE substrate at a projection angle of about 20° to about 90°, with many crystals also laying parallel to the substrate surface.

Figure 18A:
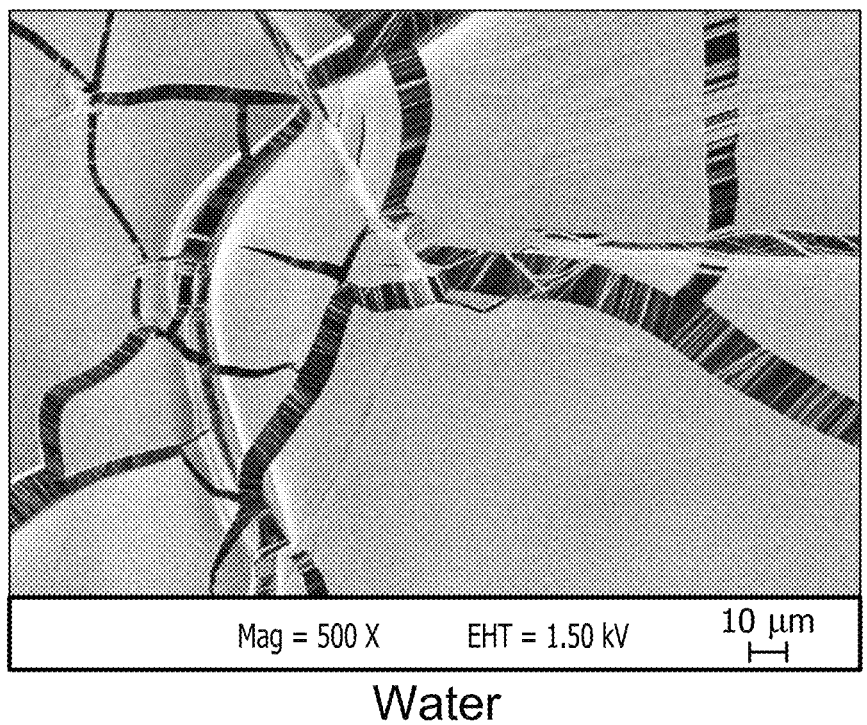
FIGS. 18A to 18B are SEM micrographs showing paclitaxel crystals of various habits coated from chloroform solvent and various vapor annealing, onto a porous substrate comprising ePTFE of microstructure comprising very highly elongated nodes interconnected by fibrils.
Figure 18B:
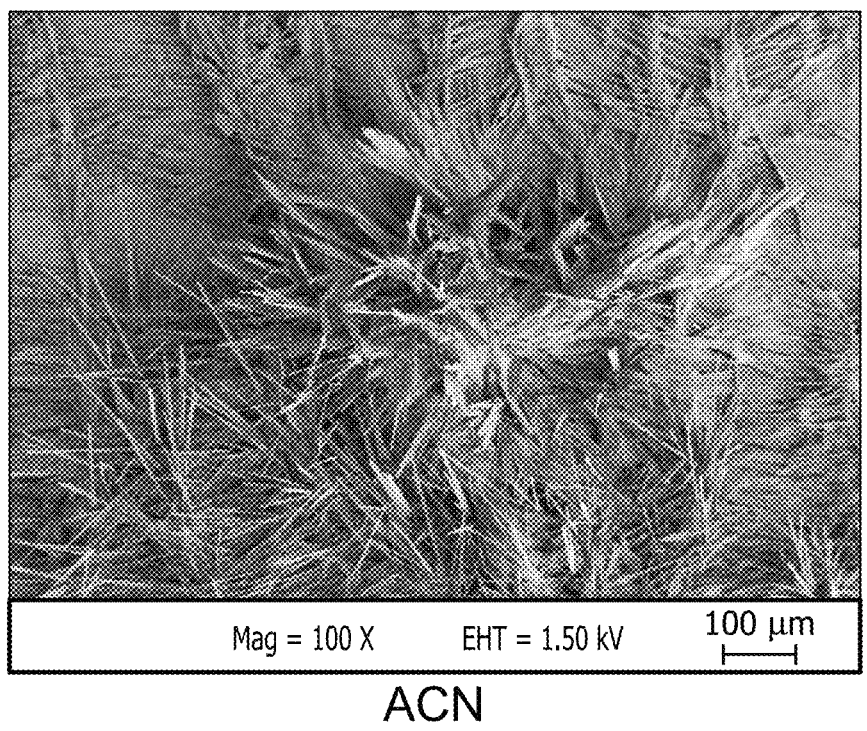

FIGS. 18A to 18B are the SEM micrographs of paclitaxel coated from chloroform (30 mg/ml) onto ePTFE of a second microstructure comprising very highly elongated nodes interconnected by fibrils.

FIG. 18A is paclitaxel coated onto ePTFE with a water vapor annealing step, and produced a smooth, continuous coating, absent of any high aspect ratio habits. The coating was cracked and separated, orienting and aligning the ePTFE fibrils, indicating the coating had penetrated into the bulk of the ePTFE substrate.

FIG. 18B is paclitaxel coated onto ePTFE with an acetonitrile vapor annealing step, and produced a plurality of paclitaxel crystals comprising acicular habits, along with numerous individual discrete crystals. The crystals were observed to penetrate into the ePTFE substrate, as indicated by elongated ePTFE nodes interconnected among the crystals. The crystals were observed to orient relative to the ePTFE substrate at a projection angle of about 20° to about 90°, with many crystals also laying parallel to the substrate surface.

In this example, a smooth glassy coating was transformed using vapor annealing into crystals that project at 20-90° relative to the substrate.

Example 14

This example describes the preparation of a porous sample substrate comprising ePTFE of a third microstructure comprising islands of PTFE or densified sections of ePTFE attached to and raised above an underlying ePTFE microstructure, further comprising drug crystals, wherein the crystals occupy the underlying ePTFE microstructure. This example further describes the utility of said coated substrate for the treatment of a tissue using said drug crystals.

An ePTFE membrane was obtained comprising a 14 layer laminate, prepared as per U.S. Pat. No. 5,641,566 to Kranzler et al., incorporated herein by reference in its entirety. The ePTFE membrane was processed using a high energy surface treatment comprising a plasma treatment followed by a heating step, as per U.S. Pat. No. 7,736,739 to Lutz et al., incorporated herein by reference in its entirety. Briefly, the ePTFE membrane was exposed to a high power atmospheric argon plasma (model #PT-2000P; Tri-Star Technologies, El Segundo, Calif.) for 3 minutes, restrained in a pin frame, then heated at 360° C. for 8 min. A representative SEM micrograph showing the microstructure of this type of ePTFE membrane is shown in cross section in FIG. 20A and in plan view in FIG. 20B. Densified ePTFE regions or plateau-like structures 2002 are shown on the raised surface of the material. Below these plateau-like structures, the node 2004 and fibril 2006 microstructure of the ePTFE underlying material can be seen. The membrane was coated with paclitaxel crystals, optionally containing urea excipient, according to Example 4.

Figure 24:
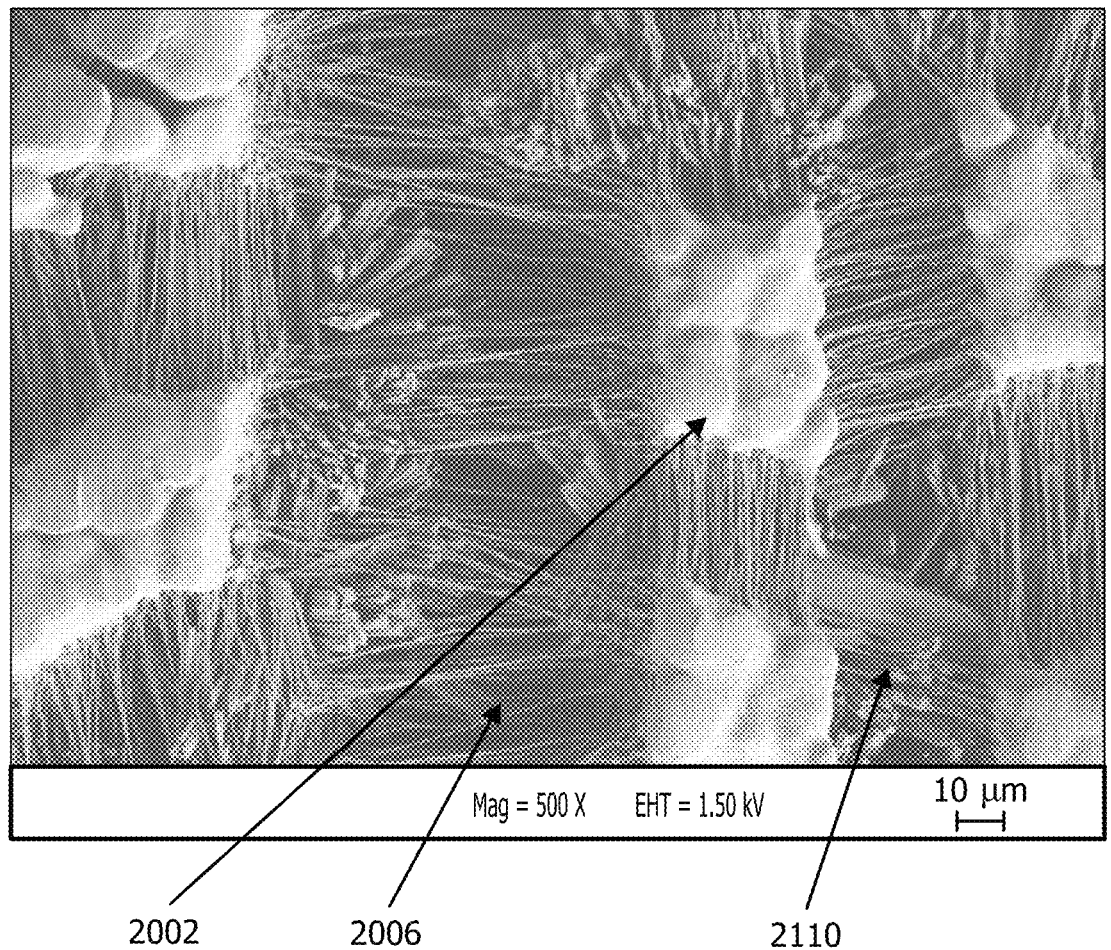
FIG. 24 is an SEM micrograph showing paclitaxel coated from methanol onto a porous substrate comprising ePTFE of a microstructure comprising islands of PTFE or densified sections of ePTFE attached to and atop an underlying ePTFE microstructure, wherein the crystals occupy the underlying ePTFE microstructure.

FIG. 24 is an SEM image of paclitaxel coated from methanol (30 mg/ml) onto an ePTFE membrane comprising ePTFE of a third microstructure comprising islands of PTFE or densified sections of ePTFE attached to and raised above an underlying ePTFE microstructure. Densification of the ePTFE to form the plateau-like structures prevented paclitaxel crystals from adhering to the plateau-like structures 2002. Instead discrete, individual crystals and crystal aggregates associated with and embedded in the underlying fibrils 2006 of the ePTFE microstructure and projected there from the angles of about 20° to about 90°.

Figure 25:
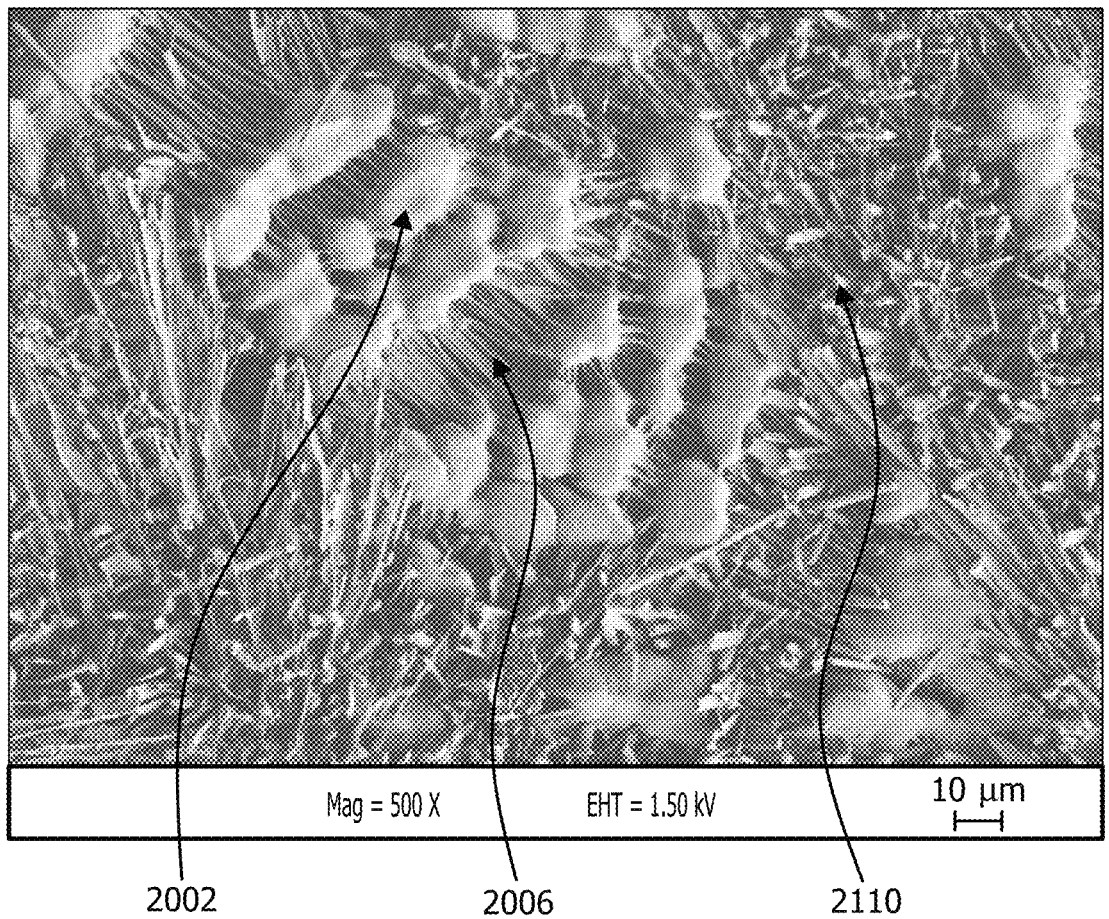
FIG. 25 is an SEM micrograph showing paclitaxel comprising a urea excipient coated from methanol onto a porous substrate comprising ePTFE of a microstructure comprising islands of PTFE or densified sections of ePTFE attached to and atop an underlying ePTFE microstructure, wherein the crystals occupy the underlying ePTFE microstructure.

FIG. 25 is an SEM image of paclitaxel coated from methanol (30 mg/ml) comprising urea excipient (8:1 mass ratio paclitaxel:urea) onto an ePTFE membrane comprising ePTFE of a third microstructure comprising islands of PTFE or densified sections of ePTFE attached to and raised above an underlying ePTFE microstructure. The paclitaxel/urea crystals did not adhere to the densified regions 2002. Instead discrete, individual crystals and crystal aggregates associated with and embedded in the underlying fibrils 2006 of the ePTFE microstructure and projected there from an angles of about 20° to about 90°.

Figure 21A:
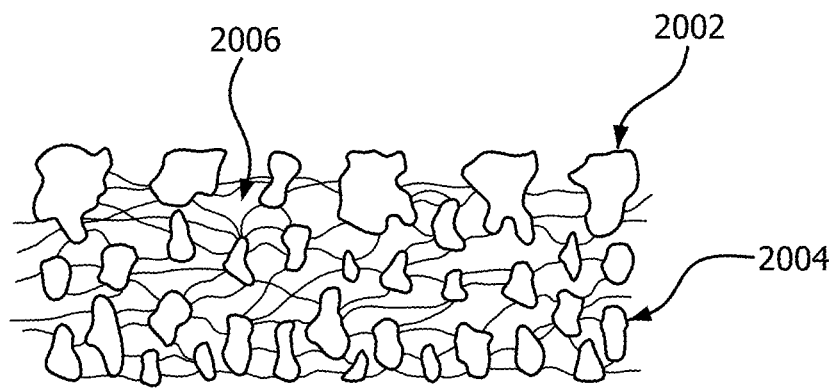
FIGS. 21A to 21C are schematics of a porous ePTFE substrate.
Figure 21B:
Figure 21C:
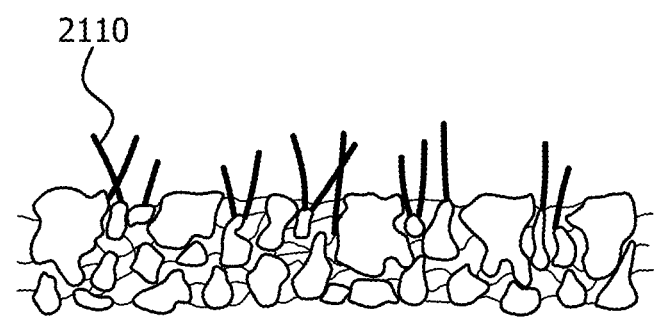

FIGS. 21A-21C are schematics of the ePTFE substrate material shown in FIGS. 20A, 20B, 24, and 25, in which densified regions 2002 of ePTFE are attached to and raised above an underlying, less dense or fibrillated ePTFE microstructure illustrated with nodes 2004 and fibrils 2006, seen in FIG. 21A, further comprising drug crystals 2110, wherein the crystals 2110 occupy the underlying ePTFE microstructure, and wherein the porous substrate is compressible in the thickness dimension whereas the projected crystals are not compressible in their axes dimension (FIG. 21B), and wherein upon compression of the porous substrate in the thickness dimension the drug crystals project from the porous substrate, as shown in FIG. 21C.

Numerous characteristics and advantages have been set forth in the preceding description, including various alternatives together with details of the structure and function of the devices and/or methods. The disclosure is intended as illustrative only and as such is not intended to be exhaustive. It will be evident to those skilled in the art that various modifications may be made, especially in matters of structure, materials, elements, components, shape, size, and arrangement of parts including combinations within the principles of the invention, to the full extent indicated by the broad, general meaning of the terms in which the appended claims are expressed. To the extent that these various modifications do not depart from the spirit and scope of the appended claims, they are intended to be encompassed therein.

What is claimed is:

1. A composite comprising:
a porous substrate having a thickness dimension comprising:
   an underlying ePTFE microstructure; and
   a plurality of dense regions coupled to the underlying ePTFE microstructure, each dense region comprising at least one of an island of PTFE or a densified section of ePTFE,
a plurality of high aspect ratio paclitaxel crystals projecting from the porous substrate at an angle of at least 20 to 90 degrees relative to the porous substrate and each having an axes dimension, a paclitaxel solution being applied onto the porous substrate having the underlying ePTFE microstructure and the dense regions and dried to form said plurality of high aspect ratio paclitaxel crystals extending at least partially into the underlying ePTFE microstructure of said porous substrate between adjacent dense regions without adhering to the dense regions,
wherein said plurality of high aspect ratio paclitaxel crystals exhibits a non-reversing endotherm at a temperature of about 215 degrees C.,
wherein the porous substrate is compressible in the thickness dimension and wherein the projected crystals are not compressible in their axes dimension,
wherein the porous substrate forms a surface of a medical device.

2. The composite of claim 1, wherein the plurality of high aspect ratio paclitaxel crystals are acicular.

3. The composite of claim 1, wherein the plurality of high aspect ratio paclitaxel crystals have a ratio such that a major dimension is at least four times the minor dimension.

4. The composite of claim 1, wherein the substrate comprises a plurality of discrete crystals.

5. The composite of claim 1, wherein the substrate comprises a plurality of crystal aggregates.

6. The composite of claim 1, wherein the ePTFE microstructure is coated with at least one of PVA, PEI, and PVP.

7. The composite of claim 1, wherein the substrate is modified by at least one of plasma treatment, corona treatment, and surfactant treatment.

8. The composite of claim 1, wherein a majority of the plurality of high aspect ratio paclitaxel crystals comprise a flat tip.

9. The composite of claim 1, wherein a majority of the plurality of high aspect ratio paclitaxel crystals comprise a jagged tip.

10. The composite of claim 1, wherein:
the dense regions are raised above the underlying ePTFE microstructure; and
the plurality of high aspect ratio paclitaxel crystals project above the dense regions.

* * * * *